United States Patent
Narayan et al.

(10) Patent No.: US 6,239,189 B1
(45) Date of Patent: May 29, 2001

(54) RADIATION-POLYMERIZABLE COMPOSITION AND PRINTING INKS CONTAINING SAME

(75) Inventors: Ramesh Narayan, Horsham; Miguel Dones, Hatfield; Theresa Miller, St. Peters, all of PA (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/049,600

(22) Filed: Mar. 27, 1998

Related U.S. Application Data

(60) Provisional application No. 60/042,284, filed on Apr. 1, 1997.

(51) Int. Cl.[7] .............................. C08F 2/50; C08L 63/10; C08L 67/07; C08L 67/08
(52) U.S. Cl. .............................. 522/40; 522/42; 522/43; 522/44; 522/64; 522/75; 522/81; 522/83; 522/101; 522/104; 522/107; 522/92; 522/90; 522/179; 522/181; 522/182; 528/295.3; 528/295.5
(58) Field of Search .............................. 522/92, 101, 90, 522/96, 97, 100, 103, 142, 141, 144, 104, 107; 525/426, 423; 528/295.3, 295.5

(56) References Cited

U.S. PATENT DOCUMENTS

| | | |
|---|---|---|
| 3,819,386 | 6/1974 | Higgins et al. . |
| 3,859,284 | 1/1975 | Formaini et al. . |
| 3,894,016 | 7/1975 | Habermeier et al. . |
| 3,952,032 | 4/1976 | Vrancken et al. . |
| 4,082,710 | 4/1978 | Vrancken et al. . |
| 4,204,010 | 5/1980 | Kramm et al. . |
| 4,218,294 | 8/1980 | Brack . |
| 4,247,426 | 1/1981 | Hinze et al. . |
| 4,270,985 | 6/1981 | Lipson et al. . |
| 4,395,524 | 7/1983 | Emmons et al. . |
| 4,425,469 | 1/1984 | Emmons et al. . |
| 4,466,994 | 8/1984 | Hubbard et al. . |
| 4,627,876 | 12/1986 | Fries et al. . |
| 4,652,492 | 3/1987 | Seiner et al. . |
| 4,778,843 | 10/1988 | Cooperman et al. . |
| 4,840,980 | 6/1989 | Pekarik . |
| 4,896,598 | 1/1990 | Leech, Jr. . |
| 4,937,296 | 6/1990 | Golownia . |
| 5,096,938 | 3/1992 | Beck et al. . |
| 5,138,027 | 8/1992 | Van Beek . |
| 5,154,760 | 10/1992 | Miller, Jr. . |
| 5,385,986 | 1/1995 | Frihart et al. . |
| 5,623,041 | 4/1997 | Boucher . |
| 5,804,671 | 9/1998 | Dones et al. . |
| 5,889,076 * | 3/1999 | Dones et al. .......................... 522/143 |

OTHER PUBLICATIONS

"Riegel's Handbook of Industrial Chemistry", Eighth Edition, Edited by James A. Kent, 1983 by Van Nostrand Reinhold Company, Inc., pp. 801–808.

Kirk–Othmer Encyclopedia of Chemical Technology, Third Edition, vol. 13, Hydrogen–ion Activity to Laminated Materials, Glass, 1981 by John Wiley & Sons, Inc., pp. 374–397.

* cited by examiner

*Primary Examiner*—Susan W. Berman
(74) *Attorney, Agent, or Firm*—John E. Drach; Martin G. Meder; Michael P. Dilworth

(57) ABSTRACT

A radiation-polymerizable composition contains at least one radiation curable acrylate resin oligomer prepared by reacting an alkoxylated polyol with a first acid component which includes an ethylenically unsaturated carboxylic acid; and a rheology modifier prepared by reacting a diepoxide with a second acid component which includes an ethylenically unsaturated carboxylic acid or reactive derivative thereof in the presence of a polyamide based on a polymerized fatty acid. The ethylenically unsaturated carboxylic acids of the first and second acid components are preferably acrylic acid or methacrylic acids. The diepoxide is preferably a diglycidyl ether such as bisphenol A. Colorants such as pigments or dyes optionally may be incorporated into the composition to form a printing ink which is curable by ultraviolet (UV) or electron beam radiation.

51 Claims, 7 Drawing Sheets

RADIATION-POLYMERIZABLE COMPOSITION AND PRINTING INKS CONTAINING SAME

CROSS REFERENCE TO RELATED APPLICATIONS

This application claims priority to U.S. Provisional Application Ser. No. 60/042,284 filed Apr. 1, 1997.

BACKGROUND

1. Field of the Invention

The present invention relates to a radiation-polymerizable composition, especially useful as or in a coating or ink, containing a radiation-curable acrylate resin oligomer component and a copolymerizable rheology modifier component. More particularly, the present invention relates to a printing ink which incorporates such a radiation-polymerizable composition.

2. Background of the Art

Printing inks generally are composed of coloring matter such as pigment or dye dispersed or dissolved in a vehicle. The ink can be a fluid or paste that can be printed onto a substrate such as paper, plastic metal, or ceramic and then dried.

Inks can be classified according to the substrate onto which the ink is intended to be applied or the method of application. For example, inks can be applied by raised type (e.g. letter press, flexographic), from a planar surface (lithographic), from a recessed surface (intaglio) or through a stencil (silk screen). Different methods of application and different substrates require different properties in the ink.

Rheology is one of the most important properties of the ink which must be suited to the substrate and manner of application. Printing inks are generally non-Newtonian fluids, which means that the rate of flow of the ink fluid is not proportional to the stress applied. Thus, some inks are required to be thixotropic, which means that the viscosity of the ink decreases with increasing agitation. Other inks are dilatant fluids in which increased agitation or rate of shear increases the viscosity and makes the ink less fluid.

The three main technologies being practiced today which make the bulk of the paints, coatings, inks and adhesive industries are solvent borne, water borne and zero volatile organic compounds (VOC). The main film forming process is either drying (evaporation of a solvent from polymer solution) or curing (two or more components reacting to form a thermosetting polymer). While the water borne systems are more environmentally friendly and acceptable from a waste and pollution standpoint, both solvent and water based systems are energy intensive, requiring drying ovens to remove the solvent or water. For several years there has been a technological push to eliminate solvents and water, i.e., to develop waterless zero VOC systems. Energy curing is one technology which has been investigated with this objective in mind. In an energy curable system, a relatively fluid formulation is instantly converted to a cross-linked polymer when exposed to energy from a visible or ultra-violet (UV) light source or an electron beam (EB). This technology reduces waste and requires less overall energy consumption. In many cases it vastly improves production speeds and produces properties such as high gloss and excellent abrasion resistance. Hence, energy curing is the technology of choice for many applications such as coatings for wood furniture, floor tiles, magazine covers, CD labels and jackets, high gloss optical fibers, electronic encapsulants and stereolithography. UV or EB curing can be accomplished by free radical, cationic, anionic, or charge transfer mechanisms.

One feature of importance to ink, as well as any other coating material, is adhesion. Inks adhere well to porous materials such as paper or cloth because, to some extent, the ink penetrates the fibers of the substrate. However, adhesion can be a problem with non-porous substrates such as plastic or metal.

Rheology modifying (RM) additives are often used in controlling the fluid flow characteristics of lithographic, letterpress and screen inks. In a press, UV cured inks experience high shear, their viscosity is reduced and they lose their optimum consistency. Inorganic additives such as silica have been used to control viscosity but they present problems such as reducing gloss in the final product and increase in viscosity over time.

SUMMARY

In accordance with the present invention, a radiation-polymerizable composition is provided which comprises a substantially homogeneous admixture of:

a) at lease one radiation-curable acrylate resin oligomer obtained by reacting an alkoxylated polyol with a first acid component which includes a first ethylenically unsaturated carboxylic acid; and, b) a rheology modifying oligomer copolymerizable with radiation curable acrylate resin oligomer (a) when subjected to radiation polymerization conditions, the rheology modifying oligomer being obtained by reacting a diepoxide with a second acid component which includes a second ethylenically unsaturated carboxylic acid or reactive derivative thereof in the presence of a polyamide derived from a polymerized fatty acid.

The foregoing composition can be used as a coating material to form a film on a substrate by applying the composition to a substrate and exposing the composition to a polymerizing radiation such as UV or electron beam radiation. Colorants such as pigments or dyes may be incorporated into the composition to provide a printing ink for use in letter press, lithography, and the like.

The rheology modifying oligomer component of the foregoing composition eliminates or reduces the need for the addition of inorganic additives and/or thickening agents and becomes an integral part of the molecular structure of the radiation-polymerized composition.

The expression "radiation-polymerizable" shall be understood herein to include polymerizing as well as curing reactions occurring in the resinous composition as the latter is exposed to a radiant energy source.

DETAILED DESCRIPTION OF PREFERRED EMBODIMENTS

Figure 1:
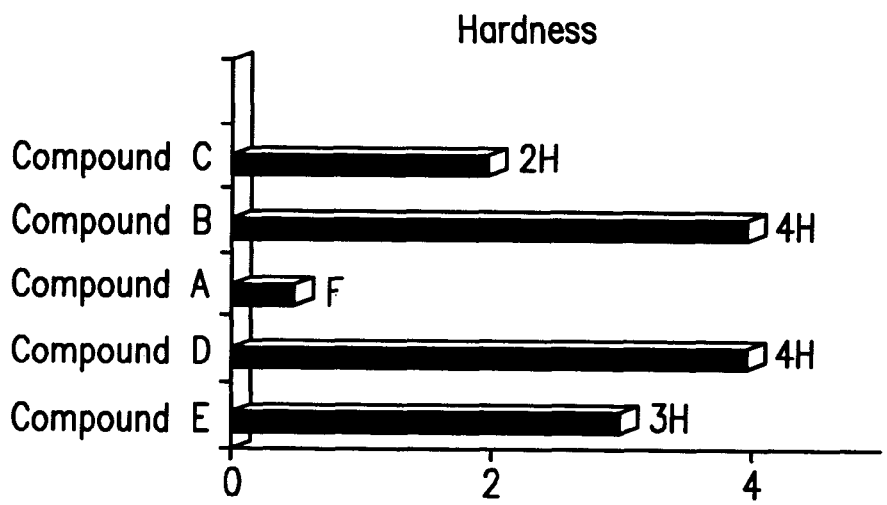
FIG. 1 is a graph showing the hardness ratings of several films derived from radiation-polymerizable compositions in accordance with the invention.

While the present invention is particularly applicable to printing inks, it should be understood that any coating material, with or without pigmentation, for printing or non-printing applications, is within its scope. Percentages of materials are by weight unless stated otherwise. Note that all quantities appearing hereinafter shall be understood to be modified by the term "about" except in the Examples and unless indicated otherwise.

The coating composition herein includes a radiation-polymerizable vehicle which imparts basic mechanical properties and serves as a binder, and at least one rheology modifying (RM) resin. Other ingredients optionally include reaction diluents, photoinitiators, wetting agents, flow and leveling agents, adhesion promoters, fillers and coloring matter such as any of the pigments or dyes currently used in inks or paints.

Acrylate resin oligomers suitable for use as vehicles in the present invention can be synthesized by esterifying an alkoxylated polyol such as propoxylated glycerol, alkoxylated trimethylolpropane, alkoxylated ditrimethylol propane and/or tris-hydroxyethyl isocyanurate and its higher alkoxylated derivatives with acrylic acid and diacid such as adipic acid, azaleic acid, sebacic acid, and dimer acid (available as EMPOL 1008 from Henkel Corp.). Other acids such as adipic, lauric, stearic may additionally be employed in the esterification reaction. Useful oligomers can possess a number average molecular weight ranging from 200 to 50,000, more preferably from 400 to 20,000, and most preferably from 500 to 10,000.

The polymerizable vehicle is preferably a UV curable acrylate resin oligomer. Examples of suitable oligomers include: low viscosity reactive diluent acrylates (e.g., PHOTOMER® 4028, available from Henkel Corp. Ambler, Pa.), high viscosity epoxy diacrylate resins (e.g., PHOTOMER® 3016, available from Henkel Corp.), fatty acid modified epoxy diacrylate (PHOTOMER® 3072), acrylated polyesters such as those described below.

Typical characteristics of such acrylated polyester resins are set forth below in Table 1:

TABLE 1

| Vehicle | Color (Gardner) | Acid Value (mg KOH/g) | Viscosity (cps) | Functionality (Theoretical) | Molecular Weight |
|---|---|---|---|---|---|
| Compound A | 3 | <20 | 2,500–4,500 | 4 | 1,300 |
| Compound B | 2 | <20 | 200,000–220,000 | 4 | 1,400 |
| Compound C | 3 | <20 | 20,000–30,000 | 6 | 1,300 |
| Compound D | 1 | <20 | 400–700 | 4 | 800 |
| Compound E | 12 | 85–90 | 7,000–10,000 | 2 | 1,000 |

Compound A, Compound B and Compound C are modified fatty acid based polyester acrylates designed with a balance of hydrophobic and hydrophilic groups in the backbone. This allows for their use in lithographic inks where such a balance is critical for in-line press performance. Compound D is designed as a general purpose resin for use in clear overprint coatings and also as a modifier for other oligomers. The viscosity of these oligomers increases by an order of magnitude each, allowing for a wide formulation latitude by blending the various resins and reactive diluents.

Compound A is an exemplary member of polyester compositions produced by the esterification of (a) a polycarboxylic member selected from the group consisting of polycarboxylic acids comprised of a diacid having more than 12 carbon atoms and reactive derivatives thereof (e.g. alkyl esters thereof wherein the alkyl group has from 1 to 4 carbon atoms), (b) an ethylenically unsaturated member selected from the group consisting of ethylenically unsaturated mono-carboxylic acids and reactive derivatives thereof, (e.g. alkyl esters thereof wherein the alkyl group thereof has from 1 to 4 carbon atoms), and (c) an ethoxylated alkanetriol having an average degree of ethoxylation per hydroxyl of less than 2 and comprised predominantly of ethoxylated alkanetriol species having one ethoxylate group per hydroxyl.

Broadly speaking, these polyesters are prepared by forming a mixture of a polycarboxylic acid or reactive derivative, an ethylenically unsaturated acid or derivative thereof, and an ethoxylated alkanetriol. The equivalent ratios of the acid groups to hydroxyl groups of the reactants should be roughly unitary so that the reaction product is predominantly comprised of species which have no free acid or hydroxyl functionality (or in the case of the use of a lower alkyl ester of a polycarboxylic acid or ethylenically unsaturated acid, no residual lower alkyl ester functionality). Further, it is preferred to use an equivalent ratio of polycarboxylic acid-:ethylenically unsaturated acid:ethoxylated alkanetriol of roughly 1:2:3. Thus, the predominant product of the reaction should be the product of "capping" the diacid at each end with the ethoxylated alkanetriol and reaction of the remaining hydroxyl groups of the ethoxylated alkanetriol with the ethylenically unsaturated acid. However, the reaction product will be a complex mixture which is further comprised of higher oligomers and unreacted or partially reacted acids and ethoxylated alkanetriols.

The polycarboxylic acid, and particularly the diacid thereof, should have the hydrophobic character of a higher fatty acid. Thus, it preferably contains polycarboxylic species having from 12 to 90 carbons atoms and more preferably from 18 to 54 carbon atoms. The polycarboxylic acid radical may be saturated or unsaturated and straight or branched. In addition to the diacid having more than 12 carbon atoms, it typically also contains species having from 1 to 6 and more typically from 1 to 4 carboxyl groups. Instead of the free acid, it is also possible to use functional derivatives, such as acid halides, anhydrides, esters, salts or the like. Typically at least 80 eq. % of the acid equivalents of the polycarboxylic acid will be contributed by the diacid, more typically at least 90 eq. %, and most typically at least 92 eq. % to 98 eq. %.

Preferred diacids having a higher alkylene chain are described in *Encyclopedia of Polymer Science and Technology*, vol. 11, pp. 476–489, (John Wiley & Sons, Inc. N.Y., N.Y., 1988), the disclosure of which is incorporated herein by reference. Such preferred diacids include dimer acids (produced by the polymerization of fatty acids, e.g. oleic acid that results in a diacid which is a divalent hydrocarbon having 36 carbon atoms), tridecanedioc acid (produced by the ozonolysis of erucic acid), $C_{19}$ diacid (produced by the hydroformylation of oleic acid with carbon monoxide) and $C_2$, diacid (produced by the reaction of tall oil fatty acid with acrylic acid). The preferred diacids are dimer acids. Dimer acids are also described in detail in U.S. Pat. No. 5,138,027 (Van Beek), the disclosure of which is incorporated herein by reference.

The term "polymerized fatty acid" is intended to be generic in nature and to refer to polymerized acids obtained from fatty acids, the composition including predominantly dimerized fatty acids, with minor amount of trimerized fatty acids and residual monomeric fatty acids. The term "fatty acids" refers to saturated, ethylenically unsaturated and acetylenically unsaturated, naturally occurring and synthetic monobasic aliphatic carboxylic acids which contain from 8 to 24 carbon atoms. While specific references are made in this application to polymerized fatty acid which are obtained from $C_{18}$ fatty acids, it will be appreciated that the methods of this invention can likewise be employed with other polymerized fatty acids.

The preferred starting acids for the preparation of the polymerized fatty acids used in this invention are oleic and linoleic acids, due to their ready availability and relative ease of polymerization. Mixtures of oleic and linoleic acids are found in tall oil fatty acids, which are a convenient commercial source of these acids. Fatty acids can be polymerized using various well known catalytic and noncatalytic polymerization methods. A typical composition of the polymerized $C_{18}$ tall oil fatty acids which are used as the starting materials for the polymerized acids which can be used in the present invention is:

| | |
|---|---|
| $C_{18}$ monobasic acids (monomer) | 0–15% by wt. |
| $C_{36}$ dibasic acids (dimer) | 60–95% by wt. |
| $C_{54}$ (or higher) trimer acid or polybasic acids | 0.2–35% by wt. |

In preparing polymerized fatty acids it is preferable that the starting polymerized fatty acid contains as high a percentage as possible of the dimer ($C_{36}$ dibasic) acid, e.g. at least 90% by wt., in order to obtain optimum physical properties in the final product.

In addition to the polymerized fatty acids, a wide variety of additional dicarboxylic acids or anhydrides of dicarboxylic acids can be used in a minor equivalent amount (e.g. from 0 to 20 equivalent percent of the total diacid equivalents) to prepare the reaction product, including aliphatic, cycloaliphatic, and aromatic dicarboxylic acids. Representative of such acids (which may contain from 2 to 22 carbon atoms) are oxalic, glutaric, malonic, adipic, succinic, suberic, sebacic, azelaic, pimelic, terephthalic, isophthalic, dodecanedioic and phthalic acids, naphthalene dicarboxylic acids, and 1,4-or 1,3-cyclohexane dicarboxylic acids. Also suitable are anhydrides such as, for example, phthalic anhydride, succinic anhydride, maleic anhydride, glutaric anhydride, octenylsuccinic anhydride, dodecenylsuccinic anhydride, chlorendic anhydride, tetrahydrophthalic anhydride, hexahydrophthalic anhydride and methyltetrahydrophthalic anhydride. The ethoxylated alkanetriol organic compound contains predominantly species having 3 hydroxyl groups in the molecule. Examples of these include glycerol, trimethylolethane, and trimethylolpropane. Adducts of alkylene oxides with alkanetriols are known substances which may be obtained by the relevant methods of preparative organic chemistry. Ethoxylation of alcohols is extensively discussed in *Encyclopedia of Polymer Science and Technology*, vol. 6, pp. 225–273, (John Wiley & Sons, Inc. N.Y., N.Y., 1986), the disclosure of which is incorporated herein by reference. On an industrial scale, they are typically produced by ethoxylation of an alkanetriol in the presence of basic catalysts, such as for example lithium hydroxide, potassium hydroxide, sodium methylate, strontium phenolate or calcined hydrotalcite, at temperatures of 120 to 180° C. and under pressures of 1 to 5 bar. After the ethoxylation, the products may be neutralized by addition of acids (phosphoric acid, acetic acid, preferably lactic acid).

In the context of this invention, it has proved to be of particular advantage to use adducts of on average 2.1 to 3.9 moles of ethylene oxide with the alkanetriol, typically on average 2.5 moles to 3.5 moles, and more typically on average 2.8 to 3.2 moles. The trimethylolpropane 3EO adducts are particularly preferred, this adduct having on average 2.9 to 3.1 moles of ethylene oxide. In this adduct, the predominant molecular species will contain three ethoxylate residues. Thus, the average degree of ethoxylation per hydroxyl group of the alkanetriol will be about 1. Further, the ethoxylated alkanetriol, should be essentially free of unethoxylated alkanetriols, e.g. typically less than 10 wt. % of the ethoxylated alkanetriol will be unethoxylated alkanetriol species, more typically less than 5% by weight. Thus, the reaction product as a whole will typically have less than 2% by weight of acrylate esters of unethoxylated alkanetriol, more typically less than 1% by weight.

The ethylenically unsaturated member selected from the group consisting of ethylenically unsaturated monocarboxylic acids and reactive derivatives thereof are typically alpha, beta-ethylenically unsaturated carboxylic acids containing from 3 to 8 carbon atoms. These acids contain one free carboxyl group or the chemical equivalent of a carboxyl group, such as an acid halide (e.g. chloride), anhydride, ester, salt or similar group. Preferred examples are acrylic acid, methacrylic acid, and the alkyl esters thereof wherein the alkyl group thereof has from 1 to 4 carbon atoms. Particularly preferred examples are acrylic acid and methacrylic acid. Such acids are described in "Acrylic and Methacrylic Acid Polymers", *Encyclopedia of Polymer Science and Engineering*, vol. 1, pp. 211–234 (John Wiley & Sons, Inc., N.Y., N.Y., 1985), the disclosure of which is incorporated herein by reference.

The relative amounts of the polycarboxylic acid, ethylenically unsaturated monocarboxylic acid, and ethoxylated alkanetriol can vary broadly, but will typically be essentially stoichiometric for the production of the "capped" product as discussed above. Thus, the equivalent ratios of polycarboxylic acid:ethylenically unsaturated acid:ethoxylated alkanetriol will typically be 1:0.5–1.5:2.5–3.5, more typically 1:0.8–1.2:2.7–3.3, and even more typically 1:0.9–1.1:2.9–3.1.

A variety of process techniques can be employed to produce fatty acid modified polyester acrylates. In a typical one-stage process, roughly stoichiometric quantities of the reactants (e.g. one mole of the diacid, two moles of the ethoxylated alkanetriol, and four moles of the ethylenically unsaturated monocarboxylic acid) are heated in an organic, water-entraining solvent (e.g. benzene, toluene or the like) in the presence of a radical polymerization inhibitor (e.g. hydroquinone, cuprous oxide or the like), an esterification catalyst (sulfuric acid, p-toluene-sulfonic acid or the like) and optionally an additive preventing the coloration of the products obtained (for example triphenyl phosphite or the like). The reaction can be carried out at atmospheric pressure, more typically at reduced pressure, typically at a temperature of 65–140° C. and for a period of 2 to 25 hours, more typically from 12 to 18 hours, with removal of the water of esterification with the aid of the solvent. The reaction is generally carried out in the presence of oxygen to inhibit polymerization of the ethylenically unsaturated acids. The reaction is carried out in the presence of a suitable inhibitor to prevent polymerization of the hydroxyalkyl acrylate double bond. These inhibitors include the monomethyl ether of hydroquinone, benzoquinone, phenothiazine, methyl hydroquinone, 2,5-di-t-butylquinone and other common free radical inhibitors known in the art. The level of inhibitor used is typically less than 2000 parts per million, e.g. 100 to 1500 parts per million. The reaction is stopped as soon as the desired degree of esterification (measured in accordance with the amount of water of esterification collected or the acid value of the product) has been reached.

After having eliminated in known manner the solvent, the catalyst, excess inhibitor and any excess of ethylenically unsaturated monocarboxylic acid, a product of the present invention is obtained, which can be used, either untreated or after a suitable purification, for its various applications.

The reaction product thus obtained is a mixture of compounds having a given molecular weight distribution, as can be shown by gel permeation chromatography, the predominant species of which is the "capped" product discussed above. This one stage process is preferred. However, it is also within the scope of this invention to employ one of the following two-stage processes. In one embodiment, under esterification conditions similar to those described for the single-stage process, the ethoxylated alkanetriol is first esterified with the polycarboxylic acid, then the residual hydroxyl groups of the ethoxylated alkanetriol are esterified with the ethylenically unsaturated monocarboxylic acid. Alternatively, the ethoxylated alkanetriol is first esterified with the ethylenically unsaturated monocarboxylic acid, then the residual hydroxyl groups of the ethoxylated alkanetriol are esterified with the polycarboxylic acid. The end products obtained from the same starting materials by the different processes mentioned above present a different molecular weight distribution as can be shown by gel permeation chromatography. One type of the molecular species that will typically be present in the reaction product will be the mono-, di-, and/or tri-ester of the ethoxylated alkanetriol and the ethylenically unsaturated monocarboxylic acid alone. These species will be present in only a minor amount. It is, however, an advantage that these species are less objectionable from a materials handling perspective as compared to the corresponding esters of an unethoxylated alkanetriol.

In the one-stage or two-stage processes described above, the free acids of the polycarboxylic acid and/or the ethylenically unsaturated monocarboxylic acid may be replaced by the halides, preferably chlorides, or anhydrides of these acids. Particularly in the case of acid halides, this makes it possible to carry out the esterification at more moderate temperatures, for example below about 40° C. In this case, it is advantageous to carry out the esterification in the presence of an acid acceptor, such as pyridine, triethylamine or the like.

In addition, the compounds described herein can also be obtained by transesterification of the ethoxylated alkanetriol with lower alkyl esters of the acids. In this case, the transesterification is carried out in a solvent having a sufficiently high boiling point (for example toluene or the like) to ensure that the reaction takes place at the boiling temperature of the mixture at an adequate speed and that an azeotropic mixture is formed with the lower alcohol freed by the transesterification. The rate of transesterification is monitored by measuring the amount of lower alcohol thus liberated, which is collected.

The reaction may be carried out at atmospheric pressure, although higher or lower pressures may be used. If the free acid form or the lower alkyl ester form of the acid reactants are employed, a by-product of the reaction will be water or lower alcohol, respectively. Removal of the by-product water or lower alcohol will tend to force the reaction to completion. Thus, distillation of such a by-product is one embodiment of the process of this invention.

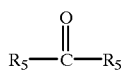

wherein $R_5$ has the formula:

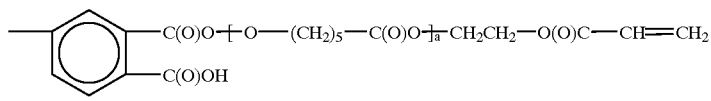

wherein a is an integer of from 2 to 20.

Compound E is an exemplary member of the class of polyester compounds having the formula:

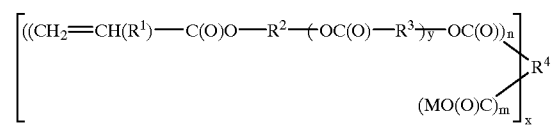

wherein:

$R^1$ is hydrogen or methyl, $R^2$ is an alkylene group or substituted alkylene group (typically having less than six carbon atoms, more typically two or three carbon atoms), R³ is an alkylene group or substituted alkylene group (typically having less than ten carbon atoms, more typically from four to six carbon atoms), R⁴ is an aromatic radical (e.g. the residue of an aromatic polycarboxylic polyanhydride having a functionality of one half the sum of n and m), M is hydrogen or a counter-ion of a salt of said compound, n and m are integers from two to four (typically two or three), x is two, and y is an integer from one to five.

Among the compounds which fall within the above formula are those in which R¹ is hydrogen, R² is an ethylene group, R³ is a pentamethylene group, and R⁴ is the residue of benzene tetracarboxylic dianhydride or benzophenone tetracarboxylic dianhydride, n and m are each two, x is one, and y is two. The compound is preferably in the form of the free acid, i.e. wherein each M is hydrogen, but may be in the form of a salt of said compound, i.e. M can be an alkali, alkaline earth or ammonium ion.

Broadly speaking, this oligomer is prepared by forming a mixture of an acrylate- or methacrylate-functional and mono-hydroxyl-functional polyester oligomer and polycarboxylic polyanhydride. These two components of the mixture then react in the presence of an esterification catalyst. The resulting product typically contains multiple ester and carboxylate functionality with the ester and carboxylate functionality being essentially equal. Further, it is preferred to use an equivalent ratio of anhydride:hydroxyl-functional acrylate of roughly 1:1. Thus, the predominant product of the reaction should be the product of "opening" each anhydride to form a diester/diacid product. However, the reaction product will typically be a complex mixture which is further comprised of residual hydroxy-functional acrylate.

The olefinically unsaturated compounds employed for the preparation of the present acryloester oligomers may be monomeric or polymeric and are characterized by the presence of a single dicarboxylic anhydride-reactive moiety such as an active hydrogen group, e.g. a hydroxyl group. Preferably, the single active hydrogen group is a hydroxyl group. Illustrative of unsaturated addition-polymerizable monomeric organic compounds having a single dicarboxylic anhydride-reactive active hydrogen group are 2-hydroxyethyl acrylate, 4-hydroxybutyl acrylate, 4-hydroxybutyl methacrylate, 2-hydroxyethyl methacrylate, 2-hydroxypropyl acrylate, 2-hydroxypropyl methacrylate, pentaerythritol triacrylate, N-hydroxymethyl acrylamide, N-hydroxymethyl methacrylamide, diethylene glycol monoacrylate, diethylene glycol monomethacrylate, glycerine dimethacrylate, trimethylol propane dimethacrylate, reaction products of polyether glycols of acrylic or methacrylic acid and the like.

The preferred olefinically unsaturated compounds are lactone-modified acrylate or methacrylate acid esters (hereinafter "lactone-acrylate adducts") prepared by reacting an appropriate lactone with an acrylate or methacrylate acid ester.

Lactones employed in the preparation of the lactone-acrylate adducts typically have the formula:

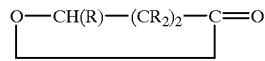

wherein R is hydrogen or an alkyl group having from 1 to 12 carbon atoms, z is from 4 to 7 and at least (z−2) of the R's is hydrogen. Preferred lactones are the epsilon-caprolactones wherein z is 4 and at least 6 of the R's are hydrogen with the remainder, if any, being alkyl groups. Preferably, none of the substituents contain more than 12 carbon atoms and the total number of carbon atoms in these substituents on the lactone ring does not exceed 12. Unsubstituted epsilon-caprolactone, i.e., where each R is hydrogen, is a derivative of 6-hydroxyhexanoic acid. Both the unsubstituted and substituted epsilon-caprolactones are available by reacting the corresponding cyclohexanone with an oxidizing agent such as peracetic acid.

Substituted epsilon-caprolactones found to be most suitable for preparing the present lactone-acrylate adducts are the various epsilon-monoalkylcaprolactones wherein the alkyl groups contain from 1 to 12 carbon atoms, e.g., epsilon-methyl-caprolactone, epsilon-ethyl-caprolactone, epsilon-propylcaprolactone and epsilon-dodecyl-caprolactone. Useful also are the epsilon-dialkylcaprolactones in which the two alkyl groups are substituted on the same or different carbon atoms, but not both on the omega carbon atoms. Also useful are the epsilon-trialkylcaprolactones wherein 2 or 3 carbon atoms in the lactone ring are substituted provided, though, that the omega carbon atom is not di-substituted. The most preferred lactone starting reactant is the epsilon-caprolactone wherein z in the lactone formula is 4 and each R is hydrogen. The acrylate or methacrylate acid esters utilized to prepare the lactone-acrylate adducts contain from 1 to 3 acrylyl or alpha-substituted acrylyl groups and one or two hydroxyl groups. Such esters are commercially available and/or can be readily synthesized. Commercially available esters include the hydroxyalkyl acrylates or hydroxyalkyl methacrylates wherein the alkyl group contains from 2 to 10 carbon atoms, preferably from 2 to 6 carbon atoms. The hydroxyalkyl acrylates and methacrylates have the following formula:

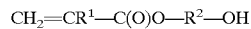

wherein R¹ is hydrogen or methyl and R² is a linear or a branched alkylene group having from 2 to 10 carbon atoms, preferably from 2 to 6 carbon atoms.

Examples of suitable hydroxyalkyl acrylates and methacrylates include 2-hydroxyethyl acrylate, 2-hydroxypropyl acrylate, 3-hydroxypropyl acrylate, 2-hydroxybutyl acrylate, 4-hydroxybutyl acrylate, 3-hydroxypentyl acrylate, 6-hydroxynonyl acrylate, 2-hydroxyethyl methacrylate, 2-hydroxypropyl methacrylate, 3-hydroxypropyl methacrylate, 2-hydroxybutyl methacrylate, 2-hydroxypentyl methacrylate, 5-hydroxypentyl methacrylate, 7-hydroxyheptyl methacrylate and 5-hydroxydecyl methacrylate.

Preferred lactone-acrylate adducts have the formula:

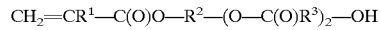

wherein R¹, R², and R³ are as described above.

The lactone-acrylate adduct is prepared by reacting the lactone with the hydroxyalkyl acrylate in the presence of less than about 200 parts per million of a catalyst. The catalysts which may be used include one or more organo-metallic compounds and other metallic compounds such as stannic chloride or ferric chloride and other Lewis or protonic acids. Preferred catalysts include stannous octoate, dibutyltin dilaurate, and other tin compounds; titanates such as tetraisopropyl titanate and butyl titanate; and the like.

The reaction is carried out at a temperature of from 100° C. to 400° C., preferably from 120° C. to 130° C. The reaction may be carried out at atmospheric pressure, although higher or lower pressures may be used. The reaction is generally carried out in the presence of oxygen to inhibit polymerization of the hydroxyalkyl acrylate. The reaction is generally carried out for a period of from 2 to 20 hours. The reaction is carried out in the presence of a suitable inhibitor to prevent polymerization of the hydroxyalkyl acrylate double bond. These inhibitors include the monomethyl ether of hydroquinone, benzoquinone, phenothiazine, methyl hydroquinone, 2,5-di-t-butylquinone, hydroquinone, benzoquinone and other common free radical inhibitors known in the art. The level of inhibitor used is less than 1000 parts per million, preferably less than 800 parts per million, and most preferably, less than 600 parts per million. A molar ratio of the lactone to hydroxyl groups in the ester of from 1:0.1 to 1:5, preferably from 1:0.3 to 1:3 is typically utilized.

An example of a lactone-acrylate adduct preferred for use in the present invention is a caprolactone-2-hydroxyethyl acrylate adduct supplied by Union Carbide Corporation under the tradename TONE M-100, which has the formula $CH_2=CH-C(O)O-CH_2-CH_2-(O-C(O)(CH_2)_5)_2-OH$.

A polycarboxylic polyanhydride aromatic compound is reacted with the lactone-acrylate adduct to introduce the ester and free carboxylate functionalities into the compound. The $R^4$ is thus an aromatic radical. Typically, $R^4$ will contain from 6 to 36 carbon atoms, more typically from 6 to 13 carbon atoms. $R^4$ will typically be a hydrocarbon group or a heterocyclic group. $R^4$ is preferably selected from the group consisting of phenyl, substituted phenyl, phenonyl (i.e. a phenyl group bearing a ketone substituent), and substituted phenonyl (e.g. benzophenonyl). In preferred embodiments, $R^4$ contains an aromatic ketone functionality, e.g. a benzophenone group or an acetophenone group.

Suitable polycarboxylic polyanhydride aromatic compounds preferably contain on average 2 to at most 4 anhydride groups. Examples of suitable such compounds are benzene tetracarboxylic dianhydride or benzophenone tetracarboxylic dianhydride.

For reaction with the polycarboxylic polyanhydride aromatic compound, a mixture thereof with the lactone-acrylate adduct is typically heated to a temperature of from 40° to 150° C. and typically 80° C., in the presence of a catalytic amount of an esterification catalyst, preferably a tertiary amine, e.g. an aromatic amine such as dimethylaminopyridine or a tri-alkyl amine, e.g. triethylamine. The amount of the anhydride equivalents of polycarboxylic polyanhydride aromatic compound will be essentially equal (e.g. 1.01:1 to 1:1.01), on an equivalents basis, to the hydroxyl equivalents of the lactone-acrylate adduct. This will produce a product which is predominantly comprised of molecules wherein the ester and free carboxylate functionality is equal.

The reaction is allowed to exotherm and is then typically heated, e.g. to a temperature of 100° C. to 140° C., more typically 120° C. to 140° C., and held for from 10 minutes to 2 hours more typically 20 minutes to one hour, until the theoretical anhydride content is <0.5% by weight as calculated, for example, from the measured acid value of the product or by spectroscopic methods (e.g. Fourier Transform Infra-Red spectroscopy), the total reaction time typically being 30 minutes to 4 hours, more typically from about one to two hours. Thereafter, the product is cooled prior to storage.

The reaction with the polycarboxylic polyanhydride aromatic compound is usually carried out at moderate temperature in the presence of a catalyst which promotes the ester-forming reaction, such as dimethylamino-pyridine.

The order of reaction is largely immaterial, it being possible to bring in the monohydric ethylenic compound either at the beginning, during the middle of the procedure, or as the last reactant. All of these variations are known in the art. It is usual herein to employ the polycarboxylic polyanhydride aromatic compound and the materials reactive therewith in stoichiometric amounts and to continue the reaction until the anhydride functionality is substantially undetectable. As will be understood, these reactions are conveniently carried out neat with reactants that are liquid at the reaction temperature or in solvent solution.

The reaction is generally carried out in the presence of oxygen to inhibit polymerization of the acrylate or methacrylate functionality. The reaction is preferably carried out in the presence of a suitable inhibitor to prevent polymerization of the acrylate or methacrylate double bond. These inhibitors include the monomethyl ether of hydroquinone, benzoquinone, phenothiazine, methyl hydroquinone, 2,5-di-t-butylquinone, hydroquinone, benzoquinone and other common free radical inhibitors known in the art. The level of inhibitor used is less than 1000 parts per million, preferably less than 800 parts per million, and most preferably, less than 600 parts per million.

The compound is preferably in the form of the free acid, i.e. wherein each M is hydrogen, but may be in the form of a salt of said compound, i.e. M can be an alkali, alkaline earth or ammonium ion. Neutralization of the free acid form of the compound with a suitable base to introduce an M counter-ion can be accomplished if desired.

The compound of the present invention can be applied to a variety of substrates. These include, for example, porous stock such as paper and cardboard, wood and wood products, metals such as aluminum, copper, steel, and plastics such as P.V.C., polycarbonates, acrylic and the like. After addition of a suitable photoinitiator, e.g., PHOTOMER 51® brand photoinitiator (benzyl dimethyl ketal), the compound is applied by methods such as spraying, rollcoating, flexo and gravure processes onto a selected substrate. The resulting coated substrate, e.g., a paper, is typically cured under a UV or electron beam radiation. The compound may optionally be mixed with other substances such as pigments, resins, monomers and additives such as anti-oxidants and rheological modifiers. It is an advantage of certain embodiments of this invention that improved adhesion to substrates, e.g. aluminum, steel, polyethylene terephthalate, and Mylar, is exhibited by such compounds of the invention as compared to compositions wherein none of the monomers contain a free carboxyl group or salt thereof.

The compound of this invention may also be formulated with other polymerizable components to form a polymerizable mixture. Typical examples of suitable monomers which can be used as a reactive diluent, are the vinyl or vinylidene monomers containing ethylenic unsaturation, and which can copolymerize with the compositions of this invention are aromatic monomers such as styrene, vinyl toluene, tertiary butyl styrene, alpha-methyl-styrene, monochlorostyrene, dichlorostyrene, divinylbenzene, ethyl vinyl benzene, diisopropenyl benzene, acrylate or methacrylate esters such as methyl acrylate, ethyl acrylate, methyl methacrylate, ethyl methacrylate, hexanediol diacrylate, nitriles such as acrylonitrile, methacrylonitrile, the vinyl esters, such as vinyl acetate and the monovinyl esters of saturated and unsaturated aliphatic, monobasic and polybasic acids, such as the vinyl esters of the following acids: propionic, isobutyric, caproic, oleic, stearic, acrylic, methacrylic, crotonic, succinic, maleic, fumaric, itaconic hexahydrobenzoic, citric, tartaric, etc., as well as the corresponding allyl, methallyl, etc., esters of the aforementioned acids, the itaconic acid monoesters and diesters, such as the methyl, ethyl, butyl esters, etc.; the maleic and fumaric acid monoesters, diesters and their amide and nitrile compounds, such as diethyl maleate, maleyl tetramethyl diamide, fumaryl dinitrile, dimethyl fumarate; cyanuric acid derivatives having at least one copolymerizable unsaturated group attached directly or indirectly to the triazine ring such as diallyl ethyl cyanurate, triallyl cyanurate, etc., ethers such as vinyl allyl ether, divinyl ether, diallyl ether, resorcinol divinyl ether, etc., diallyl chlorendate, diallyl tetrachloro phthalate, diallyl tetrabromophthalate, dibromopropargyl acrylate, as well as the partial fusible or soluble polymerizable polymers of the hereinabove listed monomers, etc. Preferred reactive diluents are the adducts of on average 1 to 3 moles of ethylene oxide and/or propylene oxide with an alkanediol, typically on average 1.5 moles to 2.5 moles, and more typically on average 1.8 to 2.2 moles, which have been reacted with a stoichiometric amount of acrylic acid, or a reactive derivative thereof, and/or methacrylic acid or a reactive derivative thereof. The hexanediol 2EO adducts are particularly preferred, this adduct having on average 1.9 to 2.1 moles of ethylene oxide. In this adduct, the predominant molecular species will contain two ethoxylate residues. Thus, the average degree of ethoxylation per hydroxyl group of the alkanetriol will be about 1. Examples of such diluents are disclosed in U.S. Pat. No. 4,382,135, the disclosure of which is incorporated herein by reference.

In preparing the polymerizable compositions of this invention containing the reaction product of this invention and one or more of the monomers of the type listed hereinabove, the relative amount of the monomers can vary broadly. In general, however, the monomer or monomers are used at less than 50% by weight of the composition, typically in the range of 10% to 30% by weight, and more typically in the range of 15% to 25% by weight.

The new derivatives of this invention can be cured or converted to the infusible state, alone or in admixture with other monomers or polymers by exposure to radiation alone or in the presence of radical generating catalysts such as benzoin, benzoin ethers, and Michler's Ketone. The free radical initiator is typically present at from 0.01% to 20% by weight of the radiation curable components. Examples of useful radiation include ultraviolet light and ionizing radiation such as generated by X-Ray machines; electron accelerators such as van de Graaf machines, travelling wave linear accelerators, particularly of the type described in U.S. Pat. No. 2,736,609, natural and synthetic radioactive material, for example cobalt 60, etc. To ensure that the composition does not prematurely polymerize, a free radical inhibitor may be added to the polymerizable composition. Examples of suitable inhibitors include hydroquinone and the methyl ether thereof or butylated hydroxy toluene at a level of from 5 ppm to 2000 ppm by weight of the polymerizable components. Additives which are particularly useful in prolonging the shelf-life of the composition can also be used, e.g. ultra-violet stabilizers such as Florstab UV-II from Kromachem.

The compositions of this invention are useful in the preparation of molded, cast, laminated and coated products as adhesives, impregnants and protective coatings. They can be used alone or with fillers, dyes, pigments, opacifiers, lubricants, plasticizers, natural or synthetic resins or other modifying bodies.

In the method of coating a substrate according to the invention, the composition, optionally containing a photoinitiator, is applied to the surface of a substrate and subsequently exposed to a radiation source until an adherent dry polymerized film is formed on the substrate. Sources of radiant energy appropriate for initiating cure of the formulations have been described extensively in the literature and are well known to those skilled in the art. These include various sources of particulate and non-particulate radiation producing wavelengths generally less than 700 nanometers. Especially useful is actinic radiation in the 180–440 nm range which can be conveniently obtained by use of one of several commercially available ultra-violet sources specifically intended for this purpose. These include low, medium and high pressure mercury vapor lamps, He—Cd and Ar lasers, xenon arc lamps, etc. Photoinitiator systems having a corresponding sensitivity to light in this wave band are normally incorporated into the formulation and upon irradiation lead to the formation of reactive species capable of initiating free radical polymerization. Similarly, free radical polymerization may be induced by exposure of the formulation to an electron beam without the use of a photoinitiator. Equipment capable of generating a curtain of electrons with energies between 150 and 300 KeV is particularly suitable for this purpose and its use is well documented in the literature.

Particularly preferred sources of radiation emit electromagnetic radiation predominantly in the ultra-violet band. When such a source is used, the polymerizable composition preferably contains a photoinitiator susceptible to ultra-violet radiation, e.g. benzoin, benzoin ethers, α,α-dimethoxy-α-phenylacetophenone, diethoxyacetophenone, α-hydroxy-α,α-dimethylacetophenone, 1-benzoylcyclohexanol, and aryl phosphine oxide based photoinitiators such as, for example, LUCERIN™ TPO available from BASF Corp.

The amount of radiation necessary to cure the composition will of course depend on the angle of exposure to the radiation, the thickness of the coating to be applied, and the amount of polymerizable groups in the coating composition, as well as the presence or absence of a free radical initiating catalyst. For any given composition, experimentation to determine the amount of radiation sensitive pi bonds not cured following exposure to the radiation source is the best method of determining the amount and duration of the radiation required. Typically, an ultra-violet source with a wavelength between 200 and 420 nm (e.g. a filtered mercury arc lamp) is directed at coated surfaces carried on a conveyor system which provides a rate of passage past the ultra-violet source appropriate for the radiation absorption profile of the composition (which profile is influenced by the degree of cure desired, the thickness of the coating to be cured, and the rate of polymerization of the composition).

Compound D can be synthesized by esterification of glycerol propoxylate with adipic acid and acrylic acid in the presence of 4-methoxyphenol, PTSA and hypophosphorous acid and has the formula:

$$(CH_2)_4-[C(O)O-CH(CH_3)-CH_2-O-CH_2-CH(OCH_2CH(CH_3)-O(O)CH=CH_2)CH_2(OCH_2CH(CH_3)-O(O)CH=CH_2]_2$$

Compound B can be prepared by reacting trishydroxyethyl isocyanurate with acrylic acid and dimer acid at 98–102° C., preferably in a solvent such as toluene or cyclohexane and in the presence of a catalyst such as para-toluene sulfonic acid (PTSA). Compound B has the following formula:

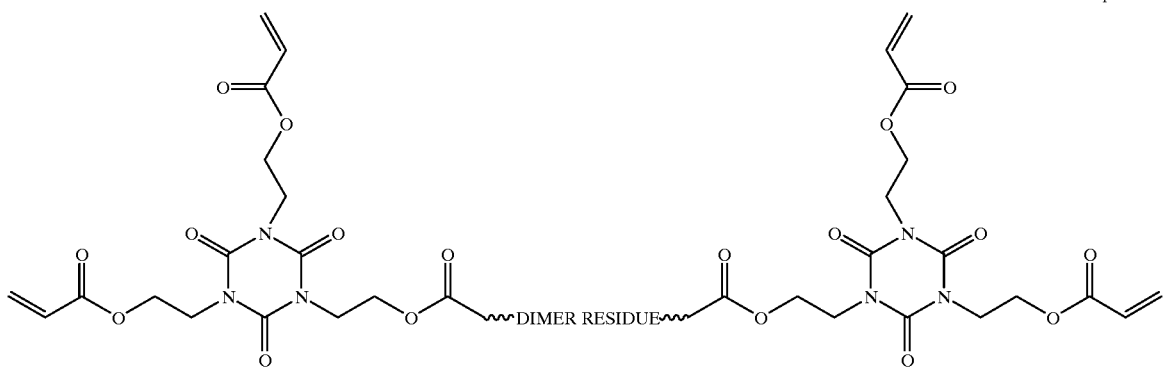

Compound B

Compound C can be prepared by reacting ditrimethylol propane with acrylic acid and dimer acid at 98–102° C., preferably in a solvent such as toluene or cyclohexane and in the presence of a catalyst such as PTSA. Compound C has the following formula:

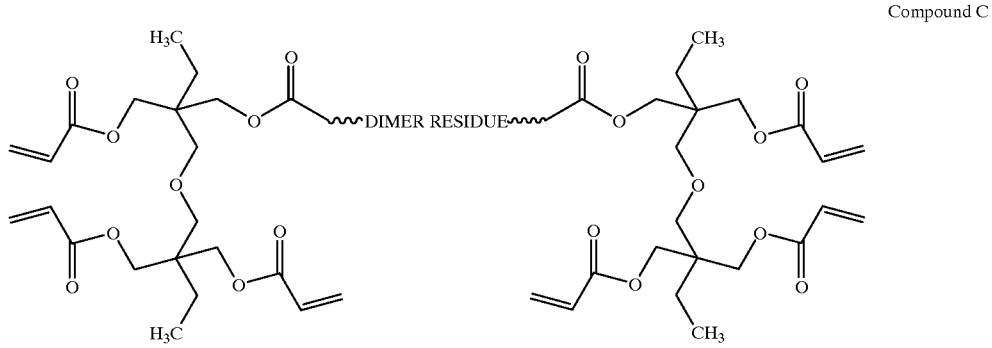

Compound C

The rheology modifying resins ("RM resins") are oligomers which are copolymerizable with the vehicle resin and impart enhanced thixotropic properties to the coating composition. That is, such RM resins undergo efficient shear thinning under high shear rates as seen, for example, in lithographic inks on a printing press. The RM resins can be made, for example, by co-reacting a polyamide (e.g., VERSAMID™ 335, available from Henkel Corp.) with an epoxy resin and acrylic acid. Typical characteristics of suitable RM resins are set forth below in Table 2:

TABLE 2

| RM Resin | Color (Gardner) | Acid Value (mg KOH/g) | Viscosity (poise, 60° C.) | Functionality (Theoretical) | Appearance |
|---|---|---|---|---|---|
| Compound F | 5 | 5 | 250–450 | 2 | yellow paste |
| Compound G | 4 | 5 | 400–600 | 2 | pale yellow paste |
| Compound H | 7 | 5 | 500–700 | 2 | yellow paste |

The RM resins listed above comprise the reaction product of a diepoxide and an acid component which includes an ethylenically unsaturated carboxylic acid or reactive derivative thereof, reacted in the presence of a polyamide derived from a polymerized fatty acid. The polyamide typically has a number average molecular weight of less than 10,000 g/mole.

Useful epoxides are the glycidyl ethers of both polyhydric phenols and polyhydric alcohols, epoxidized fatty acids or drying oil acids, epoxidized diolefins, epoxidized di-unsaturated acid esters, as well as epoxidized unsaturated polyesters, preferably containing an average of more than one epoxide group per molecule. Depending upon whether the epoxy resin is substantially monomeric or polymerized to some degree, the preferred epoxy compounds will have a molecular weight of from 300 to 600 and an epoxy equivalent weight of between 150 and 1,200.

Representative examples of the epoxides include condensation products of polyphenols and (methyl)epichlorohydrin. For the polyphenols, there may be listed bisphenol A, 2,2'-bis(4-hydroxyphenyl)methane (bisphenol F), halogenated bisphenol A, resorcinol, tetrahydroxyphenylethane, phenol novolac, cresol novolac, bisphenol A novolac and bisphenol F novolac. There may also be listed epoxy compounds of the alcohol ether type obtainable from polyols such as alkylene glycols and polyalkylene glycols, e.g. ethylene glycol, 1,2-propylene glycol, 1,3-propylene glycol, 1,4-butanediol, 1,6-hexanediol, neopentyl glycol, glycerine, polyethylene glycol, polypropylene glycol, polytetrahydrofuran, (i.e., poly(1,4-butanediol), which is obtainable under the designation TERATHONE™ from DuPont), and alkylene oxide-adduct of bisphenols, and (methyl)epichlorohydrin; glycidyl amines obtainable from anilines such as diaminodiphenylmethane, diaminophenylsulfone and p-aminophenol, and (methyl)epichlorohydrin; glycidyl esters based on acid anhydrides such as phthalic anhydride and tetrahydro-or hexahydro-phthalic anhydride; and alicyclic epoxides such as 3,4-epoxy-6-methylcyclohexylmethyl and 3,4-epoxy-6-methylcyclohexyl carboxylate.

Glycidyl polyethers of polyhydric phenols are made from the reaction of a polyhydric phenol with epihalohydrin or glycerol dihalohydrin, and a sufficient amount of caustic alkali to combine with the halogen of the halohydrin. Glycidyl ethers of polyhydric alcohols are made by reacting at least about 2 moles of an epihalohydrin with 1 mole of a polyhydric alcohol such as ethylene glycol, pentaerythritol, etc., followed by dehydrohalogenation.

In addition to polyepoxides made from alcohols or phenols and an epihalohydrin, polyepoxides made by the known peracid methods are also suitable. Epoxides of unsaturated esters, polyesters, diolefins and the like can be prepared by reacting the unsaturated compound with a peracid. Preparation of polyepoxides by the peracid method is described in various periodicals and patents and such compounds as butadiene, ethyl linoleate, as well as di- or tri-unsaturated drying oils or drying oil acids, esters and polyesters can all be converted to polyepoxides. Epoxidized drying oils are also well known, these polyepoxides usually being prepared by reaction of a peracid such as peracetic acid or performic acid with the unsaturated drying oil according to U.S. Pat. No. 2,569,502.

In certain embodiments, the diepoxide is an epoxidized triglycerides containing unsaturated fatty acids. The epoxidized triglyceride may be produced by epoxidation of one or more triglycerides of vegetable or animal origin. The only requirement is that a substantial percentage of diepoxide compounds should be present. The starting materials may also contain saturated components. However, epoxides of fatty acid glycerol esters having an iodine value of 50 to 150 and preferably 85 to 115 are normally used. For example, epoxidized triglycerides containing 2% to 10% by weight of epoxide oxygen are suitable. This epoxide oxygen content can be established by using triglycerides with a relatively low iodine value as the starting material and thoroughly epoxidizing them or by using triglycerides with a high iodine value as starting material and only partly reacting them to epoxides. Products such as these can be produced from the following fats and oils (listed according to the ranking of their starting iodine value): beef tallow, palm oil, lard, castor oil, peanut oil, rapeseed oil and, preferably, cottonseed oil, soybean oil, train oil, sunflower oil, linseed oil. Examples of typical epoxidized oils are epoxidized soybean oil with an epoxide value of 5.8 to 6.5, epoxidized sunflower oil with an epoxide value of 5.6 to 6.6, epoxidized linseed oil with an epoxide value of 8.2 to 8.6 and epoxidized train oil with an epoxide value of 6.3 to 6.7.

Further examples of polyepoxides include the diglycidyl ether of diethylene glycol or dipropylene glycol, the diglycidyl ether of polypropylene glycols having molecular weight up to, for example, 2,000, the triglycidyl ether of glycerine, the diglycidyl ether of resorcinol, the diglycidyl ether of 4,4'-isopropylidene diphenol, epoxy novolacs, such as the condensation product of 4,4'-methylenediphenol and epichlorohydrin and the condensation of 4,4'-isopropylidenediphenol and epichlorohydrin, glycidyl ethers of cashew nut oil, epoxidized soybean oil, epoxidized unsaturated polyesters, vinyl cyclohexene dioxide, dicyclopentadiene dioxide, dipentene dioxide, epoxidized polybutadiene and epoxidized aldehyde condensates such as 3,4-epoxycyclohexyl methyl-3',4'-epoxycyclohexane carboxylate.

Particularly preferred epoxides are the glycidyl ethers of bisphenols, a class of compounds which are constituted by a pair of phenolic groups inter-linked through an intervening aliphatic bridge. While any of the bisphenols may be used, the compound 2,2-bis (p-hydroxyphenyl) propane, commonly known as bisphenol A, is more widely available in commerce and is preferred. While polyglycidyl ethers can be used, diglycidyl ethers are preferred. Especially preferred are the liquid Bisphenol A-epichlorohydrin condensates with a molecular weight in the range of from 300 to 600.

The acid component is comprised of an ethylenically unsaturated acid. Particularly suitable ethylenically unsaturated monocarboxylic acid are the alpha, beta-unsaturated monobasic acids. Examples of such monocarboxylic acid monomers include acrylic acid, beta-acryloxypropionic acid, methacrylic acid, crotonic acid, and alpha-chloroacrylic acid. Preferred examples are acrylic acid and methacrylic acid. Also suitable acid components are adducts of hydroxyalkyl acrylates or hydroxyalkyl methacrylates and the anhydrides of dicarboxylic acids such as, for example, phthalic anhydride, succinic anhydride, maleic anhydride, glutaric anhydride, octenylsuccinic anhydride, dodecenylsuccinic anhydride, chlorendic anhydride, tetrahydrophthalic anhydride, hexahydrophthalic anhydride and methyltetrahydrophthalic anhydride. Such adducts can be prepared by methods of preparative organic chemistry known in the art. The acid component can also contain other carboxylic acids. In certain embodiments, the acid component will be comprised of a minor amount, e.g. less than 50% of the total acid equivalents, more typically less than 20% of the total acid equivalents, of a fatty acid. The fatty acids are saturated and/or unsaturated aliphatic monocarboxylic acids containing 8 to 24 carbon atoms or saturated or unsaturated hydroxycarboxylic acids containing 8 to 24 carbon atoms. The carboxylic acids and/or hydroxycarboxylic acids may be of natural and/or synthetic origin. Examples of suitable monocarboxylic acids are caprylic acid, 2-ethylhexanoic acid, capric acid, lauric acid, myristic acid, palmitic acid, palargonic acid, palmitoleic acid, stearic acid, isostearic acid, oleic acid, elaidic acid, petroselic acid, linoleic acid, linolenic acid, elaeostearic acid, conjuene fatty acid, ricinoleic acid, arachic acid, gadoleic acid, behenic acid, erucic acid and brassidic acid and the technical mixtures thereof obtained, for example, in the pressure hydrolysis of natural fats and oils, in the oxidation of aldehydes from Roelen's oxo synthesis, or as monomer fraction in the dimerization of unsaturated fatty acids. In a particularly preferred embodiment, the fatty acid is derived from technical mixtures of the fatty acids mentioned which are obtainable in the form of the technical mixtures typically encountered in oleochemistry after the pressure hydrolysis of oils and fats of animal or vegetable origin, such as coconut oil, palm kernel oil, sunflower oil, rape oil, rapeseed oil and coriander oil and beef tallow. However, the fatty acid may also contain a branched fatty acid residue, for example the residue of 2-ethyl hexanoic acid, isopalmitic acid or isostearic acid.

Preferred fatty acids are mixtures obtained from natural sources, e.g. palm oil, palm kernel oil, coconut oil, rapeseed oil (from old high-erucic acid plants or from new low-erucic acid plants, a.k.a. canola oil), sunflower oil (from old low-oleic plants or from new high-oleic plants), castor oil, soybean oil, cottonseed oil, peanut oil, olive oil, olive kernel oil, coriander oil, castor oil, meadowfoam oil, chaulmoogra oil, tea seed oil, linseed oil, beef tallow, lard, fish oil and the like. Naturally occurring fatty acids typically are present as triglycerides of mixtures of fatty acids wherein all fatty acids have an even number of carbon atoms and a major portion by weight of the acids have from 12 to 18 carbon atoms and are saturated or mono-, di-, or tri-unsaturated.

The preferred epoxy resins, i.e., those made from bisphenol A, will have two epoxy groups per molecule. Thus, the product of a reaction with acrylic or methacrylic acid will contain an epoxy (meth)acrylate compound having a main chain of polyepoxide and both terminals of a (meth)acrylate group, respectively. Accordingly, the stoichiometric amount of acrylic acid to form a diacrylate adduct would be two moles of acid for each two epoxy groups. In practice, however, it is preferred to use an amount of acid slightly in excess of the amount necessary to cover both epoxy groups. Therefore, the amount of acrylic acid reacted is typically between 2.001 moles to 2.1 moles, and more typically between 2.01 and 2.05 moles of acid per two epoxy groups.

The reaction of the epoxide and the acid takes place in the presence of a polyamide derived from a polymerized fatty acid. The polyamide preferably has a number average molecular weight of less than 10,000 grams/mole. Low melting polyamide resins melting within the approximate range of 90° C. to 130° C. may be prepared from polymeric fatty acids and aliphatic polyamines. Typical of the polyamines which may be used are ethylene diamine, diethylene triamine, triethylene tetramine, tetraethylene pentamine, 1,4-diaminobutane, 1,3-diaminobutane, hexamethylene diamine, piperazine, isophorone diamine, 3-(N-isopropylamine)-propylamine, 3,3'-iminobispropylamine, and the like. A preferred group of these low melting polyamides are derived from polymeric fatty acids, and ethylene diamine and are solid at room temperature.

Suitable such polyamides are commercially available under the trade designation of VERSAMID polyamide resins, e.g. VERSAMID 335, 750 and 744, and are amber-colored resins having a number average molecular weight up to 10,000, preferably from 1,000 to 4,000 and a softening point from below room temperature to 190° C.

The preferred polyamide is VERSAMID 335 polyamide which is commercially available from Henkel Corporation and has an amine value of 3, a number average molecular weight of 1699, as determined by gel permeation chromatography (GPC) using a polystyrene standard, and a polydispersity of 1.90.

The preparation of such VERSAMID polyamide resins is well known and by varying the acid and/or functionality of the polyamine, a great variety of viscosities, molecular weights and levels of active amino groups spaced along the resin molecule can be obtained. Typically, the VERSAMID polyamide resins useful herein have amine values from 0 to 25, preferably 0 to 10, more preferably 0 to 5; viscosities of from about 1 to 30 poises (at 160° C.) and polydispersities of less than 5. The amine value and number average molecular weight of the polyamide can be determined as described in U.S. Pat. No. 4,652,492 (Seiner, et. al.), the disclosure of which is incorporated herein by reference.

The polyamide is incorporated into the composition in an amount not exceeding 50% by weight based on the combined weight of the epoxide and acid components and the polyamide. Preferably, an amount not exceeding 25% by weight is utilized and most preferred is an amount of from 5% to 15% by weight.

The reaction between the epoxide and acid can be performed over a wide range of temperatures, e.g. from 40° C. to 150° C., more typically from 50° C. to 130° C. and preferably between 90° C. and 110° C., at atmospheric, sub-atmospheric or superatmospheric pressure; preferably in an inert atmosphere. Esterification is continued until an acid number of 2 to 15 is obtained. This reaction ordinarily takes place in 8 to 15 hours. To prevent premature or undesirable polymerization of the product or the reactants, it is advantageous to add a vinyl inhibitor to the reaction mixture. Suitable vinyl polymerization inhibitors include tert-butylcatechol, hydroquinone, 2,5-ditertiarybutylhydroquinone, hydroquinonemonoethyl ether, etc. Advantageously, the inhibitor is included in the reaction mixture at a concentration of 0.005 to 0.1% by weight based on the total of the reagents.

The reaction between the epoxide and the acid proceeds slowly when uncatalyzed, and can be accelerated by suitable catalysts which preferably are used, such as, for example, the tertiary bases such as triethyl amine, tributylamine, pyridine, dimethylaniline, tris (dimethylaminomethyl)-phenol, triphenyl phosphine, tributyl phosphine, tributylstilbine; alcoholates such as sodium methylate, sodium butylate, sodium methoxyglycolate, etc.; quaternary compounds such as tetramethylammonium bromide, tetramethylammonium chloride, benzyl-trimethylammonium chloride, and the like. At least 0.01 percent, based on total weight of reagents, preferably at least 0.1 percent, of such catalyst is desirable.

Typical examples of suitable monomers which can be used and added to the reaction mixture before or during the reaction, or added after the reaction, as a reactive diluent, are the vinyl or vinylidene monomers containing ethylenic unsaturation, and which can copolymerized with the compositions of this invention are, styrene, vinyl toluene, tertiary butyl styrene, alpha-methyl-styrene, monochlorostyrene, dichlorostyrene, divinylbenzene, ethyl vinyl benzene, diisopropenyl benzene, methyl acrylate, ethyl acrylate, methyl methacrylate, ethyl methacrylate, acrylonitrile, methacrylonitrile, the vinyl esters, such as vinyl acetate and the monovinyl esters of saturated and unsaturated aliphatic, monobasic and polybasic acids, such as the vinyl esters of the following acids: propionic, isobutyric, caproic, oleic, stearic, acrylic, methacrylic, crotonic, succinic, maleic, fumaric, itaconic hexahydrobenzoic, citric, tartaric, etc., as well as the corresponding allyl, methallyl, etc., esters of the aforementioned acids, the itaconic acid monoesters and diesters, such as the methyl, ethyl, butyl esters, etc.; the maleic and fumaric acid monoesters, diesters and their amide and nitrile compounds, such as diethyl maleate, maleyl tetramethyl diamide, fumaryl dinitrile, dimethyl fumarate; cyanuric acid derivatives having at least one copolymerizable unsaturated group attached directly or indirectly to the triazine ring such as diallyl ethyl cyanurate, triallyl cyanurate, etc., ethers such as vinyl allyl ether, divinyl ether, diallyl ether, resorcinol divinyl ether, etc., diallyl chlorendate, diallyl tetrachloro phthalate, diallyl tetrabromophthalate, dibromopropargyl acrylate, as well as the partial fusible or soluble polymerizable polymers of the hereinabove listed monomers, etc.

In preparing the polymerizable compositions containing the reaction product of this invention and one or more of the monomers of the type listed hereinabove, the relative amount of the monomers can vary broadly. In general, however, the monomer or monomers are used at less than 50% by weight of the composition, typically in the range of about 1% to 30% by weight, and more typically in the range of 5% to 15% by weight.

The new derivatives of this invention can be cured or converted to the infusible state, alone or in admixture with other monomers or polymers by exposure to radiation alone or in the presence of radical generating catalysts such as benzoin, benzoin ethers, and Michler's Ketone. The free radical initiator is typically present at from 0.01 to 20% by weight of the radiation curable components. Examples of useful radiation include ultraviolet light and ionizing radiation such as generated by X-Ray machines; electron accelerators such as van de Graaf machines, travelling wave linear accelerators, particularly of the type described in U.S. Pat. No. 2,736,609, natural and synthetic radioactive material, for example cobalt 60, etc. To ensure that the composition does not prematurely polymerize, a free radical inhibitor may be added to the polymerizable composition. Examples of suitable inhibitors include hydroquinone and the methyl ether thereof or butylated hydroxy toluene at a level of from 5 ppm to 2000 ppm by weight of the polymerizable components. Additives which are particularly useful in prolonging the shelf-life of the composition can also be used, e.g. ultra-violet stabilizers such as Florstab UV-II from Kromachem.

Compound H can be prepared by reacting bisphenol-A-diglycidyl ether with acrylic acid, a $C_{12}$–$C_{18}$ fatty alkyl acid and VERSAMIDE 335 polyamide and includes a compound having the formula:

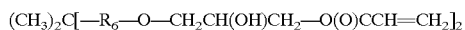

along with a polyamide grafted derivative thereof.

Compound F can be prepared by reacting bisphenol-A-diglycidyl ether with acrylic acid, 1,4-butanediol diglycidyl ether, and VERSAMIDE 335 polyamide and includes compounds having the formulas:

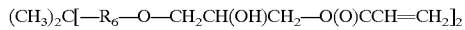

and

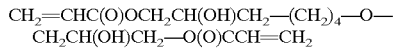

along with polyamide grafted derivatives thereof.

Compound G can be prepared by reacting bisphenol-A-diglycidyl ether with acrylic acid, and VERSAMIDE 335 polyamide and includes a compound having the formula:

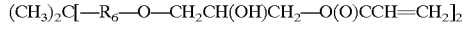

The important film properties of cured UV film are hardness, solvent resistance and adhesion. These are provided in FIGS. 1 to 3. The hardness of UV cured films of these oligomers varies from a relatively soft Compound A to relatively hard Compound D (FIG. 1). Among the fatty acid modified oligomers, Compound B gives the hardest film. This may be due to the alicyclic nature of the polyol used in this oligomer. The difference in hardness between Compound D, Compound C, and Compound A can be attributed to the higher acrylate equivalents in Compound D and Compound C which gives a denser cross linked network.

Figure 2:
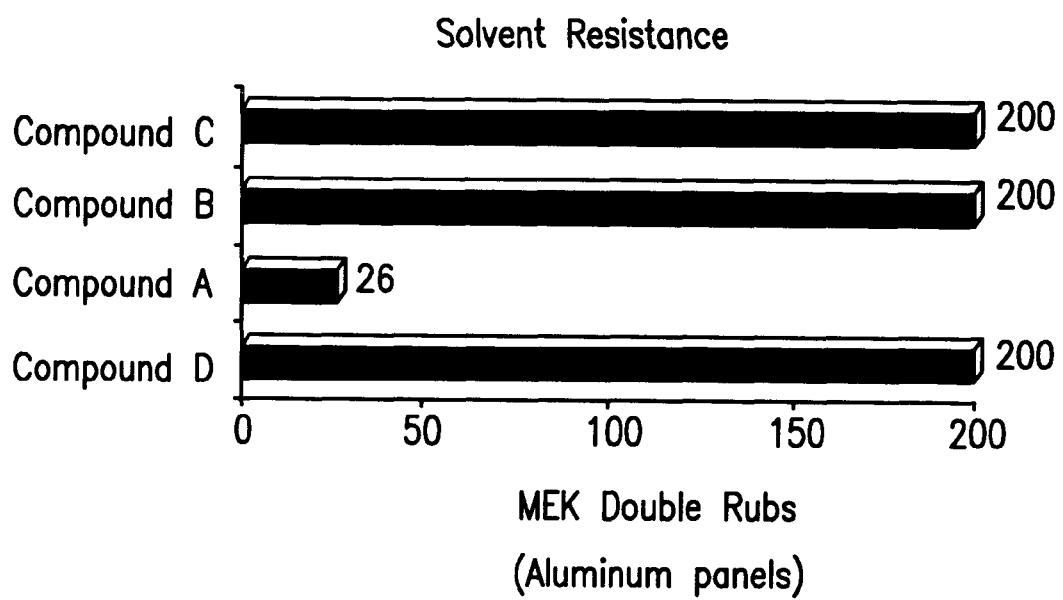
FIG. 2 is a graph showing the solvent (methyl ethyl ketone) resistance of films derived from radiation-polymerizable compositions in accordance with the invention.

The solvent resistance of UV cured films follows the same general trend (FIG. 2). The high methyl ethyl ketone (MEK) resistance of all of the oligomers except Compound A is due in part to the hydrophobicity of the polyesters which resist swelling by MEK, a polar solvent, and in part to the formation of a dense cross-linked network which resists diffusion of the solvent into the polymer chains. The trend in polarity of the polyesters listed above is as follows: Compound E>>Compound A, Compound D, >>Compound B, Compound C.

Figure 3:
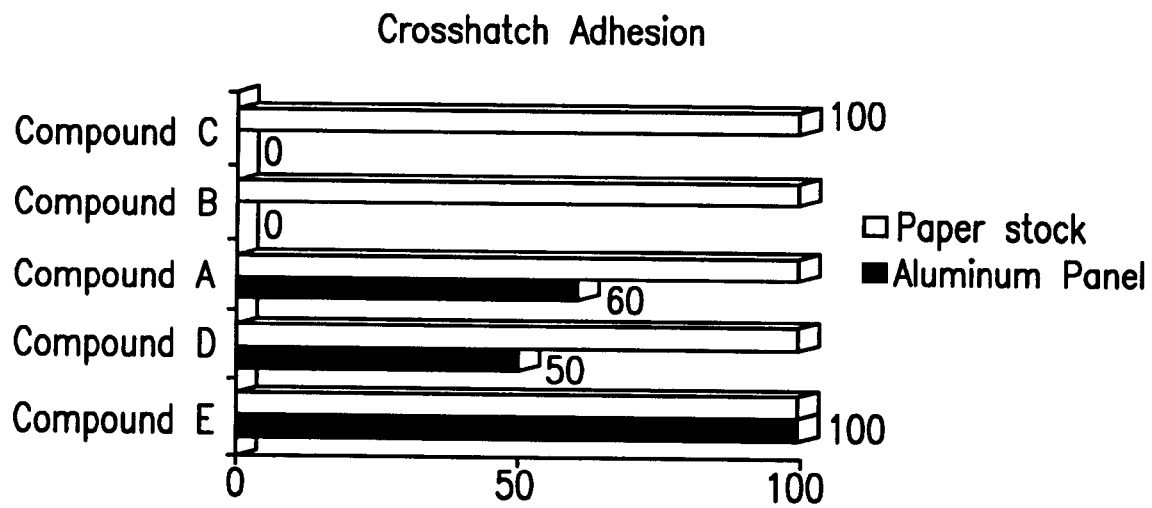
FIG. 3 is a graph showing adhesion to substrates of films derived from radiation-polymerizable compositions in accordance with the invention.
Figure 4:
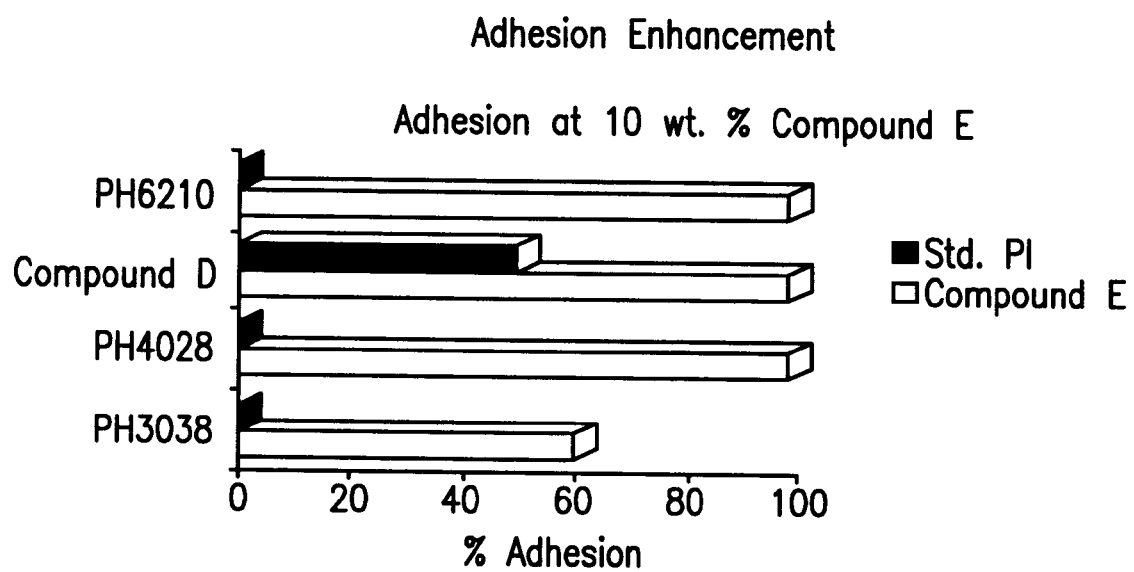
FIG. 4 is a graph showing adhesion enhancement attained by a radiation-polymerizable compositions in accordance with the invention.

The adhesion to paper stock of the acrylate resin oligomers is excellent. Adhesion to aluminum can be moderate to poor. Compound D and Compound A by virtue of their higher polarity bind to aluminum better than their more hydrophobic counterparts. The rapidity of cross-linking reactions and the volume shrinkage produced as a result leads to poor adhesion in UV cured polymers (FIG. 3). However, Compound E alleviates this problems in clear coatings. This product has built-in photoinitiator residues that self-initiate polymerization when present as is, or in conjunction with other monomers and oligomers. It also has acidic groups which increase polarity of the formulations and enhance adhesion to metals. Finally, the two acrylate groups co-polymerize with other UV curable components in the formulation. This means that the initiator residues after photolysis remain covalently bonded in the cross-linked polymer. Formulations containing this product may have potential use in applications such as radiation-polymerizable coatings for food packaging where the migratory tendencies of the photolyzed initiator residues may present practical problems. As compared with the use of a standard photoinitiator, Compound E dramatically improves adhesion when present in reactive diluents (PHOTOMER 4028), acrylated polyester (Compound D), acrylated epoxide (PHOTOMER 3038) and acrylated urethane (PHOTOMER 6210) oligomers (FIG. 4).

Figure 5:
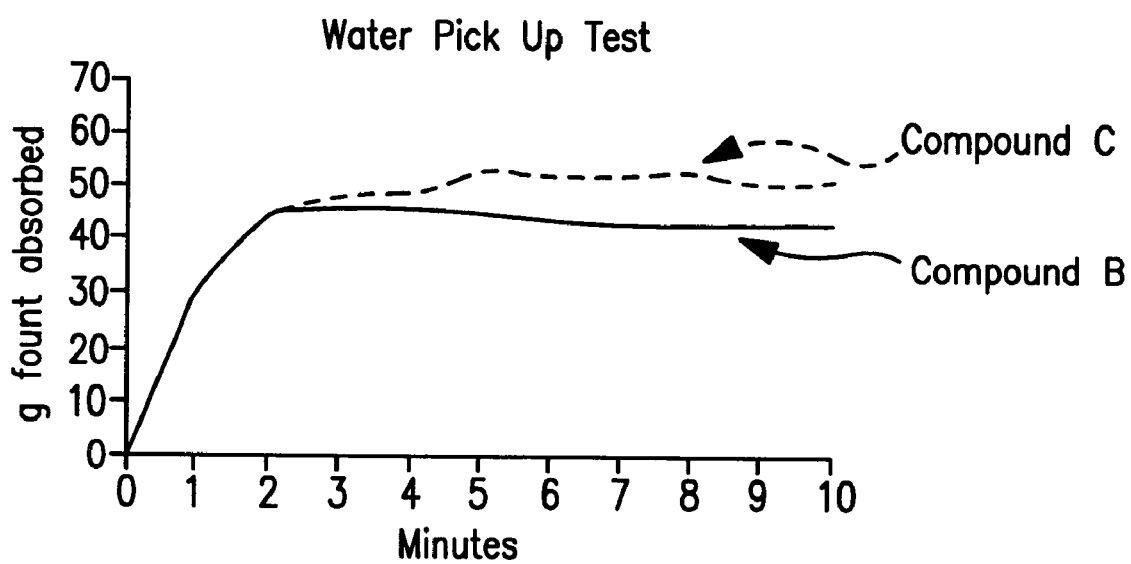
FIG. 5 is a graph showing the respective water pickup of radiation-polymerizable compositions in accordance with the invention.

Colorants are optional components of the coating material and can be in the form of insoluble finely ground pigments or soluble dyes. For example, phthalo blue pigment ground to a particle size range of from about 1–4 microns (as measured on a Hegmann gauge) is suitable for use in combination with the oligomer vehicles described above. Compound B and Compound C wet the phthalo blue pigment very well. Further, in lithographic inks the formation of an oil in water emulsion is a key step in obtaining optimal press performance. To determine this a test of water pick-up called the Surland test can be conducted for pigmented formulations. The Surland test involves measuring the amount and rate of water uptake under low shear conditions. Further information regarding this test may be found in The Printing Manual, R. H. Leach and J. Pierce (eds.), Chapman and Hall, New York, pg. 368 (1993). Referring now to FIG. 5, which shows the water pick-up properties of Compound B and Compound C, both oligomers exhibit similar rates of water pick-up in the linear portion of the graph. Both oligomers exhibit rapid pick-up of water initially and then reach equilibrium. This is indicative of a satisfactory lithographic ink.

The following examples are given for the purpose of illustrating the present invention. All parts and percentages of composition are by weight unless stated otherwise.

EXAMPLE 1

Compound A is a compound having the formula:

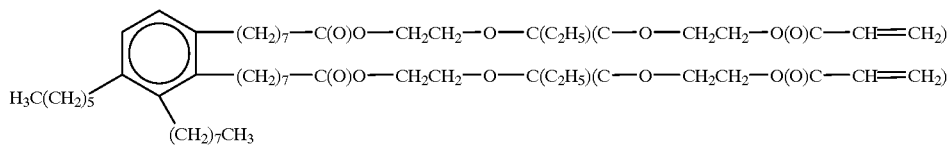

and is made in accordance with the following procedure:

Charge a reactor with 156.88 grams of the three mole ethoxylate of trimethylolpropane (eq. wt. 63.75 grams/eq.), 180.12 grams of a dimer acid (eq. wt. 282.47 grams/eq.) having a content of about 94% by wt. dimer acids, about 2.5% by wt. higher polymerized acids, and about 3.5% by wt. of monomeric fatty acids, available from Henkel Corp. as EMPOL 1008, and 91.82 grams of acrylic acid (eq. wt. 282.47), 218.69 grams of toluene, 0.13 grams of hydroquinone (200 ppm) as a polymerization inhibitor, 0.52 grams of hydroquinone monomethyl ether (800 ppm) as a polymerization inhibitor, and 3.28 grams of hypophosphorous acid as a color reducer. Sparge reactor with air and 25 ml/minute. Heat the reactor contents to 55–60° C. and charge 8.56 grams of para-toluenesulfonic acid (2% by wt. of combined weights of acids and ethoxylated trimethylolpropane). Heat contents of reactor to 98° C. Continue heating until rate of reaction slows as measured by collection of water of esterification. Apply mild vacuum in steps of 2 in. of Hg starting at 4–6 in. of Hg. Maintain reaction temperature at 95–98° C. Apply vacuum no greater than 16–18 in. of Hg. After 6 hours of reaction check acid value of product every 2 hours. After 10–12 hours check acid value of product every hour. Reaction is complete when acid value of the product is less than 12. Cool reactor to ambient temperature. Add toluene sufficient to make a reactant:solvent ratio of 1:1 by weight, calculated by initial batch weight less theoretical amount of water collected. Warm reactor to 40° C. Charge reactor with a solution of caustic saline (that contains 0.5 wt. % sodium hydroxide and 16 wt. % sodium chloride) in an amount equal to 20% of the batch weight less theoretical water of esterification. Mix by slow stirring for 3–5 minutes and then let phases split. Let stand at 45–50° C. for about 30 minutes and decant aqueous phase. Measure acid value of organic phase. Repeat caustic saline wash as necessary to reduce acid value to 4–5. Warm organic phase to 40° C. Charge reactor with a solution of saline (that contains 16 wt. % sodium chloride) in an amount equal to 20% of the batch weight less theoretical water of esterification. Mix by slow stirring for 3–5 minutes and then let phases split. Let stand at 45–50° C. for about 30 minutes and decant aqueous phase. Make a solution of the same amounts of hydroquinone and methyl hydroquinone as charged earlier in 5 ml of isopropanol and 5 ml of toluene. Charge to reactor and heat contents to 50° C. Sparge reactor with air at 30 ml/minute and apply vacuum to 29–30 in. of Hg to distill toluene. Increase temperature in steps to 82° C. Do not exceed 85° C. Continue distillation until toluene is less than 10 ppm by head space gas chromatography. Stir hot product with 1 wt. % filter aid such as powdered clay (e.g., Celite® brand available from Celite Corp.) and filter.

EXAMPLE 2

Compound E and film derived therefrom were prepared in accordance with the following method:

Benzophenone tetracarboxylic dianhydride in an amount of 24.58 parts by weight (76.3 mmole) was mixed with 52.3 parts by weight (152.6 mmole) of caprolactone-2-hydroxyethyl acrylate adduct supplied by Union Carbide Corporation under the tradename TONE M-100, 0.76 parts by weight (6.22 mmole) of dimethylamino-pyridine, and 0.19 parts by weight of methyl hydroquinone. The mixture was stirred vigorously, sparged with dry air and gradually heated to 80° C. An initial exotherm of about 10° C. was noticed. A portion of the benzophenone tetracarboxylic dianhydride appeared to be undissolved. The mixture was then heated to 110° C. to 120° C. in about 30 minutes. The undissolved material then dissolved and the solution cleared to a dark orange color. Heating was discontinued and 22.17 parts by weight of hexanediol diacrylate was added with stirring until the solution was again homogeneous. The acid value of the product should be from 80 to 95 meq/g KOH. The product was then cooled. The composition was drawn down on paper to effect a 1 mil dry film thickness and photocured.

EXAMPLE 3

Compound B was prepared in accordance with the same procedure as set forth above in Example 1 except that the following reactants and amounts were charged to the reactor:

| | |
|---|---|
| Trishydroxyethyl isocyanurate | 91.96 g |
| EMPOL 1008 | 79.54 g |
| Acrylic acid | 55.76 g |
| p-Toluene sulfonic acid | 4.54 g |
| Methyl hydroquinone | 0.28 g |
| Hydroquinone | 0.07 g |
| Hypophosphorous acid (50% aq.) | 1.16 g |
| Toluene | 114.92 g |

EXAMPLE 4

Compound C was prepared in accordance with the same procedure as set forth above in Example 1 except that the following reactants and amounts were charged to the reactor:

| | |
|---|---|
| Ditrimethylol propane | 207.64 g |
| EMPOL 1008 | 97.75 g |
| Acrylic acid | 209.60 g |
| p-Toluene sulfonic acid | 10.30 g |
| Methyl hydroquinone | 0.56 g |
| Hydroquinone | 0.14 g |
| Hypophosphorous acid (50% aq.) | 3.50 g |
| Toluene | 173.68 g |

EXAMPLE 5

Three lithographic inks were formulated using Photomer 3016 (high viscosity epoxy diacrylate) and Photomer 3072 (fatty acid modified epoxy diacrylate) as the base resins and phthalo blue pigment. Ink $A_1$ contained no RM resin. Ink $B_1$ contained 18% Compound H as an RM resin. Ink $C_1$ contained no RM resin but had 1.8% silica as a thixotropic additive. The rheological tests were conducted on a Carri-Med CSL 100 Rheometer using the cone and plate method. For the viscosity temperature profiles, the samples were prestressed at 6500 dynes/cm$^2$ and the viscosity was measured between 25° and 50° C. For shear stress measurements the samples were equilibrated at 25° C. before performing a stress sweep.

Figure 6:
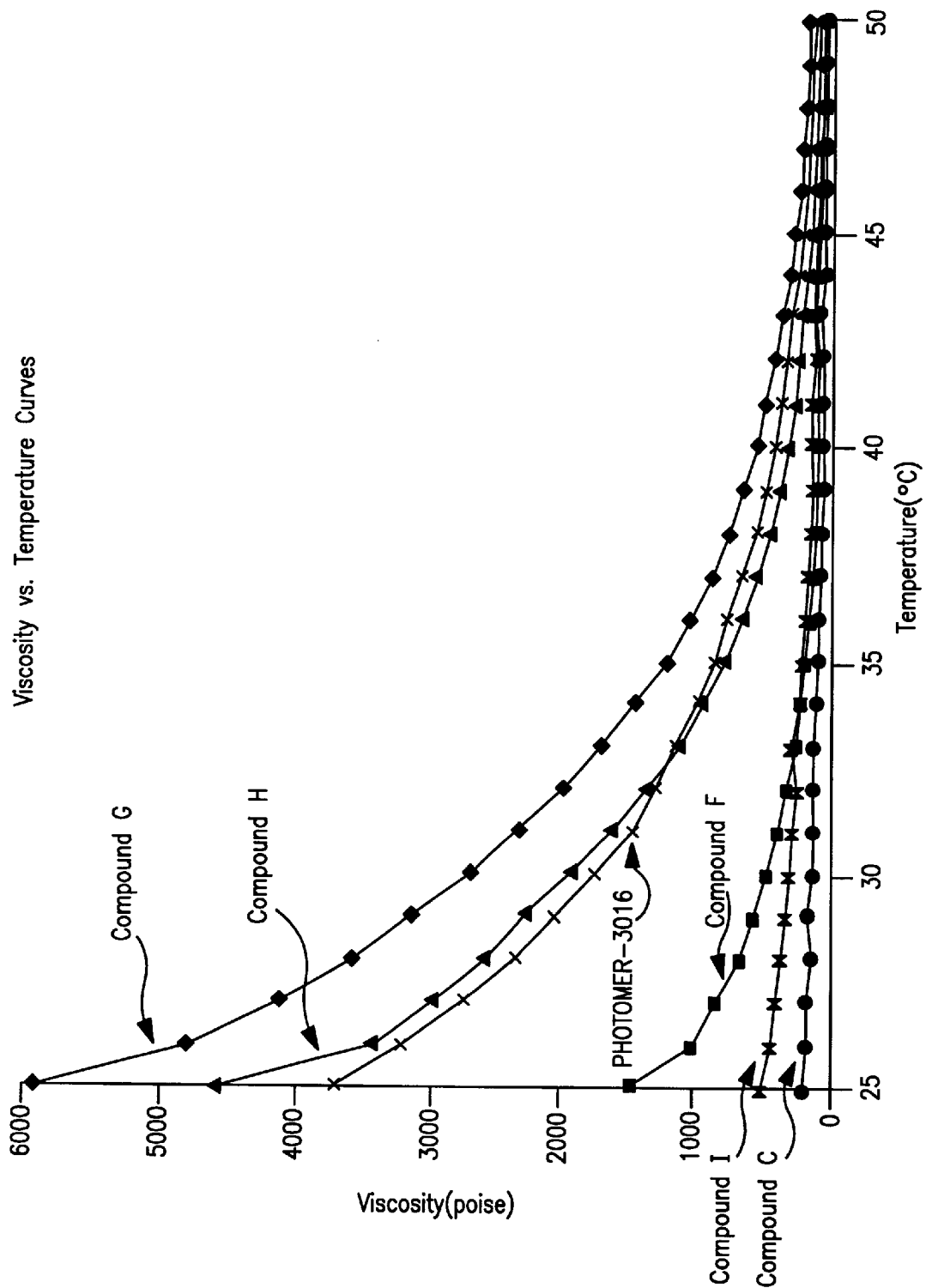
FIG. 6 is a graph showing the relationship of viscosity vs. temperature of radiation-polymerizable compositions in accordance with the invention.
Figure 7:
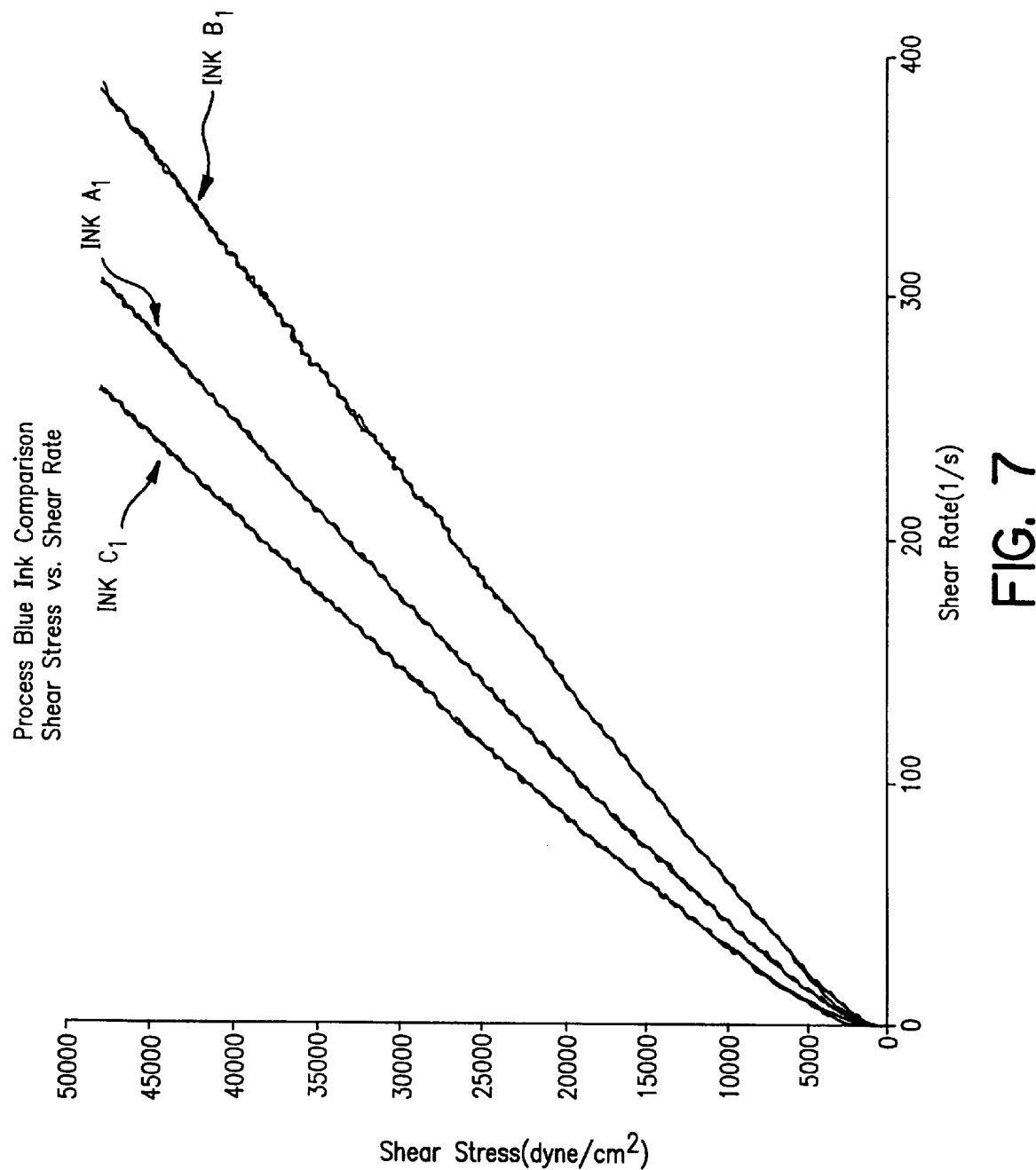
FIG. 7 is a graph showing the relationship of shear stress vs. shear rate for an ink composition containing a rheology modifying resin in accordance with the invention as compared to inks containing no rheology modifying resin.
Figure 8:
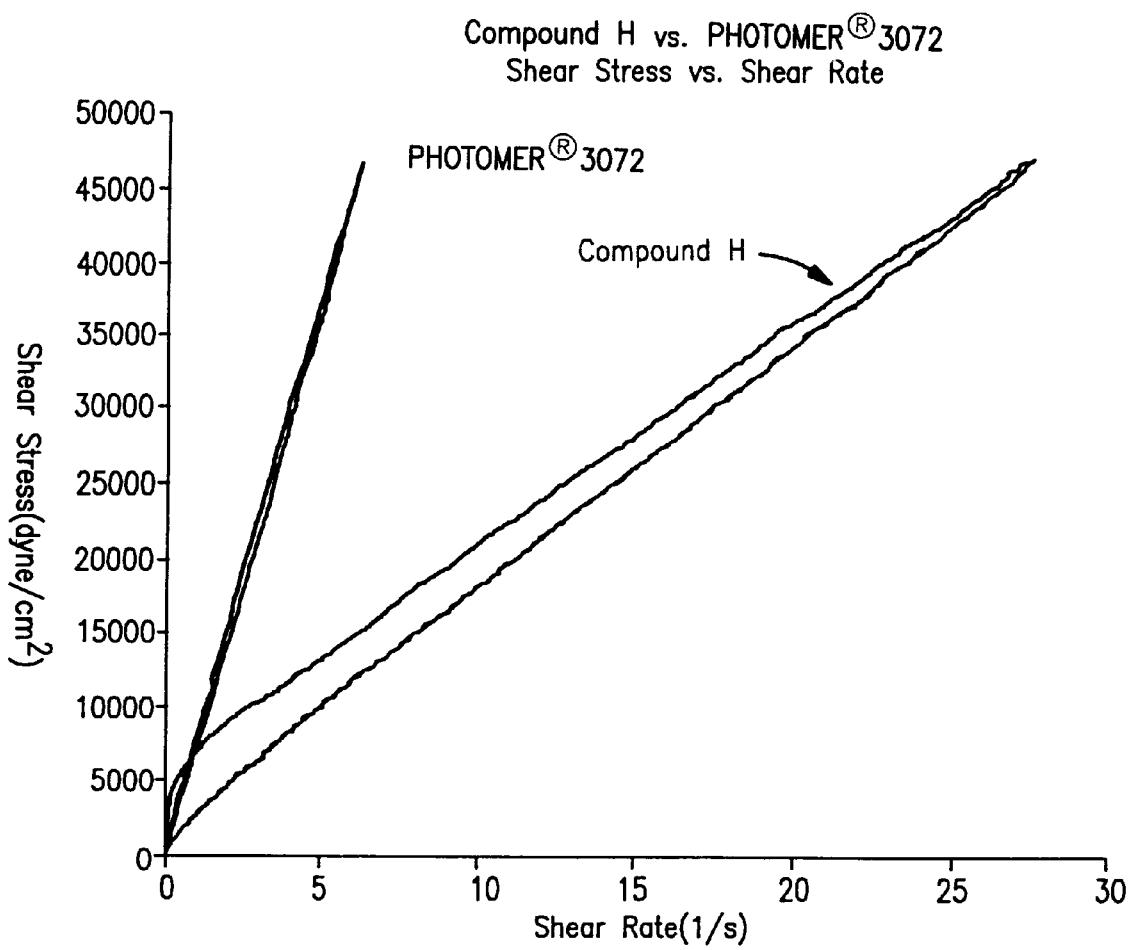
FIG. 8 is a graph showing the relationship of shear stress vs. shear rate for a certain rheology modifying resin as compared to rheology modifying oligomer prepared in accordance with the present invention as compared to a fatty acid modified epoxy diacrylate oligomer.

Except for Compound F the rheology modifying resins show a higher viscosity profile in the temperature range of 25–45° C. as compared to other acrylated oligomers Compound C (polyester acrylate) and Compound I (aromatic urethane acrylate) as shown in FIG. 6. A comparison of stress-shear sweeps of Compound H and Photomer 3072 shows pseudoplastic behavior in both resins, as shown in FIG. 8. However, the RM resin Compound H has a wider hysteresis loop, which indicates pronounced thixotropy in this resin. Thus, when RM resins are used as rheology modifiers the higher initial viscosity of these resins allows the maintenance of gel structure in inks before thinning out due to in-press shear. When the shear is removed (e.g., by transfer of the ink to the substrate) the inks regain the gel structure. The enhanced performance of RM resins in pigmented (blue ink) systems is evident in the shear-stress sweeps shown in FIG. 7. Among the inks tested, $B_1$ containing the RM resin Compound H experienced the lowest shear stress as shear rate increases. In contrast, the silica containing ink $C_1$ experienced the higher shear stress even at low shear rates. This could be detrimental to ink performance causing unwanted dot gain in printed matter.

Figure 9:
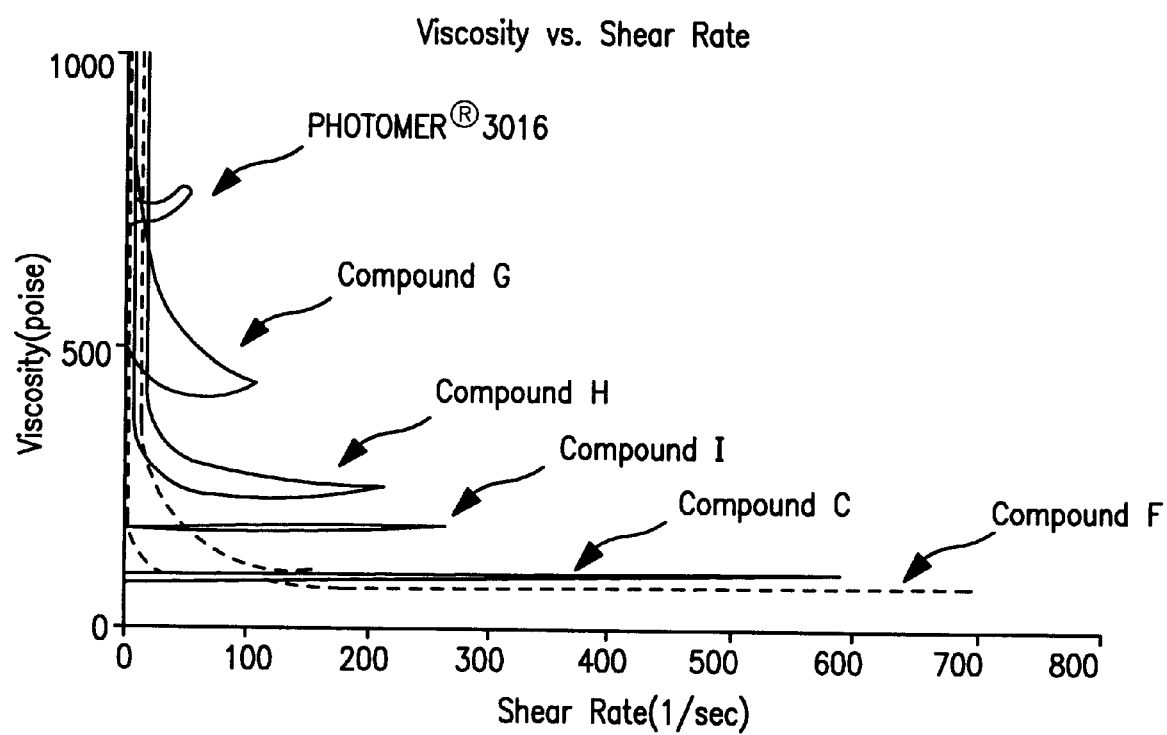
FIG. 9 is a graph showing the relationship of viscosity vs. shear rate for radiation-polymerizable compositions in accordance with the present invention as compared to a high viscosity epoxy diacrylate.

FIG. 9 is a graph showing the viscosity reduction at higher shear rates for RM oligomers Compound F and Compound G in comparison with other radiation-polymerizable oligomers and Photomer 3016. Such oligomers obviate the need for common but cumbersome inorganic fillers such as talc and silica.

Thus, acrylated polyesters Compound D and Compound A have a good overall combination of cured film properties. With proper formulating they can be used in both inks and in clear coatings for wood, paper, and plastics. Compound E self initiates UV curing and dramatically improves adhesion in clear coatings with all classes of oligomers and reactive diluents. Self curing UV resin obviates the need for photosensitizers such as benzophenone which can leave odor causing by-products in the resin. Thus, a radiation-polymerizable composition containing vehicle resin and RM resin can be formulated without significant mounts of additives which would not form a chemically bonded part of the polymer structure when cured. The higher viscosity oligomers Compound B and Compound C have good hydrophilic-lipophilic balance and can be used in lithographic, screen, letterpress and flexographic UV inks as the base resin. The rheology modifying resins impart improved in-press and functional benefits to UV inks without the need for silica and other inorganic additives.

U.S. Pat. Nos. 3,952,032 and 4,082,710, both of which are herein incorporated by reference, disclose the use of compounds with multiple acrylic radicals as photopolymerizable binders in ultra-violet curable inks and coatings. Other components of the ink composition disclosed in these patents include inert polymers and plasticizers, pigments and inorganic fillers, photoinitiators and various other conventional additives for inks, many of which may also be used in the present invention. The rheological behavior of the ink of the present invention may be modified by such fillers as long as the fillers do not react with the photoinitiators.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A radiation-polymerizable composition which comprises the product of combining:
   a) at least one radiation curable acrylate resin oligomer obtained by reacting an alkoxylated polyol with a first acid component which includes an ethylenically unsaturated carboxylic acid or reactive derivative thereof, and a polycarboxylic acid or reactive derivative thereof; and,
   b) a rheology modifier oligomer copolymerizable with radiation curable acrylate resin oligomer (a) when subjected to radiation polymerization conditions, the rheology modifying oligomer being obtained by reacting a diepoxide with a second acid component which includes an ethylenically unsaturated carboxylic acid or reactive derivative thereof in the presence of a polyamide derived from a polymerized fatty acid.

2. The composition of claim 1 wherein the ethylenically unsaturated carboxylic acid or reactive derivative thereof of the first and second acid components is selected from the group consisting of acrylic acid, methacrylic acid, adducts of hydroxyalkyl acrylates or hydroxyalkyl methacrylates and anhydrides of dicarboxylic acids.

3. The composition of claim 1 wherein said diepoxide is a diglycidyl ether.

4. The composition of claim 1 wherein said diepoxide is a diglycidyl ether of a dihydric phenol.

5. The composition of claim 1 wherein said diepoxide is a diglycidyl ether of bisphenol A.

6. The composition of claim 1 wherein said diepoxide is a diglycidyl ether of a member selected from the group consisting of alkylene glycols and polyalkylene glycols.

7. The composition of claim 1 wherein said diepoxide is a diglycidyl ether of a member selected from the group consisting of ethylene glycol, 1,2-propylene glycol, 1,3-propylene glycol, 1,4-butanediol, 1,6-hexanediol, neopentyl glycol, glycerine, polytetrahydrofuran, polyethylene glycols, and polypropylene glycols.

8. The composition of claim 1 wherein said diepoxide is an epoxidized triglyceride comprised of unsaturated fatty acids.

9. The composition of claim 1 wherein said diepoxide is an epoxidized triglyceride comprised of unsaturated fatty acids containing 2 to 10% by weight of epoxide oxygen.

10. The composition of claim 1 wherein said diepoxide is an epoxidized oil selected from the group consisting of fats and oils derived from beef tallow, palm oil, lard, castor oil, peanut oil, rapeseed oil, cottonseed oil, soybean oil, train oil, sunflower oil, and linseed oil.

11. The composition of claim 1 wherein said diepoxide is an epoxidized oil selected from the group consisting of soybean oil, train oil, sunflower oil, and linseed oil.

12. The composition of claim 1 wherein said second acid component is further comprised of a member selected from the group consisting of saturated aliphatic monocarboxylic acids containing 8 to 24 carbon atoms, unsaturated aliphatic monocarboxylic acids containing 8 to 24 carbon atoms, saturated hydroxycarboxylic acids containing 8 to 24 carbon atoms, and unsaturated hydroxycarboxylic acids containing 8 to 24 carbon atoms.

13. The composition of claim 1 wherein said second acid component is further comprised of a member selected from the group consisting of fatty acids having an even number of carbon atoms and a major portion by weight of the acids have from about 12 to 18 carbon atoms, wherein all fatty acids are saturated or mono-,di-, or tri-unsaturated.

14. The composition of claim 1 wherein said second acid component is further comprised of lauric acid.

15. The composition of claim 1 wherein said polyamide has a number average molecular weight of up to about 10,000.

16. The composition of claim 1 wherein said polyamide has a number average molecular weight of from about 1,000 to about 4,000.

17. The composition of claim 1 wherein said polyamide has a melting point in the range of about 90° C. to about 130° C.

18. The composition of claim 1 wherein said polyamide is derived from polymeric fatty acids and ethylene diamine.

19. The composition of claim 1 wherein said polyamide has an amine value from 0 to about 25.

20. The composition of claim 1 wherein said polyamide has an amine value from 0 to about 5.

21. The composition of claim 1 further including at least one additive selected from the group consisting of colorants, photoinitiators and fillers.

22. The composition of claim 1 further including a photoinitiator.

23. The composition of claim 22 wherein the photoinitiator is selected from the group consisting of benzyl dimethyl ketal, benzoin, benzoin ethers, α,α-dimethoxy-α-phenylacetophenone, diethoxyacetophenone, α-hydroxy-α,α-dimethylacetophenone, 1-benzoylcyclohexanol, and aryl phosphine oxide based photoinitiators.

24. The composition of claim 1 further including a filler.

25. The composition of claim 1 wherein the composition does not contain a significant amount of any additive which is not chemically bondable with radiation curable acrylate resin oligomer (a).

26. The composition of claim 1 wherein the polycarboxylic acid possesses more than 12 carbon atoms.

27. The composition of claim 1 wherein the polycarboxylic acid is a dicarboxylic acid.

28. The composition of claim 27 wherein the dicarboxylic acid is a dimer acid.

29. The polymerized composition resulting from the radiation-polymerization of the polymerizable composition of claim 1.

30. A film comprising a copolymerized binder resin and rheology modifying resin, wherein the binder resin is derived from at least one radiation-polymerizable acrylate resin oligomer obtained by reacting an alkoxylated polyol with a first acid component which includes an ethylenically unsaturated carboxylic acid or reactive derivative thereof, and a polycarboxylic acid or reactive derivative thereof, and the rheology modifying resin is derived from an oligomer prepared by reacting a diepoxide with a second acid component which includes an ethylenically unsaturated carboxylic acid or reactive derivative thereof in the presence of a polyamide derived from a polymerized fatty acid.

31. The film of claim 30 wherein the ethylenically unsaturated carboxylic acid of the first and second acid components is selected from the group consisting of acrylic acid and methacrylic acid.

32. The film of claim 30 wherein said diepoxide is a diglycidyl ether.

33. The film of claim 30 wherein said diepoxide is a diglycidyl ether of bisphenol A.

34. The film of claim 30 wherein said diepoxide is a diglycidyl ether of a member selected from the group consisting of alkylene glycols and polyalkylene glycols.

35. The film of claim 30 further containing a colorant.

36. The film of claim 30 wherein said film does not contain a significant amount of any additive which is not chemically bondable with the binder resin.

37. The film of claim 30 wherein the polycarboxylic acid possesses more than 12 carbon atoms.

38. The film of claim 30 wherein the polycarboxylic acid is a dicarboxylic acid.

39. The film of claim 38 wherein the dicarboxylic acid is a dimer acid.

40. A method for forming a coating on a substrate, comprising:
  a) providing a radiation-polymerizable composition which contains the product of combining at least one radiation curable acrylate resin oligomer prepared by reacting an alkoxylated polyol with a first acid component which includes an ethylenically unsaturated carboxylic acid or reactive derivative thereof, and a polycarboxylic acid or reactive derivative thereof, and a rheology modifying oligomer copolymerizable with the radiation curable acrylate resin oligomer when subjected to radiation-polymerization conditions, the rheology modifying oligomer being obtained by reacting a diepoxide with a second acid component which includes an ethylenically unsaturated carboxylic acid or reactive derivative thereof in the presence of a polyamide derived from a polymerized fatty acid;
  b) applying said composition to a substrate; and
  c) exposing said composition to a source of radiation to effect polymerization thereof.

41. The method of claim 40 wherein said radiation is selected from ultraviolet radiation and electron beam radiation.

42. The method of claim 40 wherein the ethylenically unsaturated carboxylic acid is selected from the group consisting of acrylic acid, methacrylic acid, adducts of hydroxyalkyl acrylates or hydroxyalkyl methacrylates and anhydrides of dicarboxylic acids.

43. The method of claim 40 wherein said diepoxide is a diglycidyl ether.

44. The method of claim 40 wherein said diepoxide is a diglycidyl ether of bisphenol A.

45. The method of claim 40 wherein the composition further includes a colorant.

46. The method of claim 40 wherein the composition further includes a photoinitiator.

47. The method of claim 40 wherein the composition does not contain any additive which is not chemically bondable with the radiation curable acrylate resin oligomer.

48. A coated substrate prepared in accordance with the method of claim 40.

49. The method of claim 40 wherein the polycarboxylic acid possesses more than 12 carbon atoms.

50. The method of claim 40 wherein the polycarboxylic acid is a dicarboxylic acid.

51. The method of claim 50 wherein the dicarboxylic acid is a dimer acid.

* * * * *